United States Patent
Lo et al.

(10) Patent No.: US 10,457,990 B2
(45) Date of Patent: Oct. 29, 2019

(54) ACCURATE DEDUCTION OF FETAL DNA FRACTION WITH SHALLOW-DEPTH SEQUENCING OF MATERNAL PLASMA

(71) Applicant: The Chinese University of Hong Kong, Shatin (CN)

(72) Inventors: Yuk-Ming Dennis Lo, Homantin (CN); Peiyong Jiang, Shatin (CN); Kwan Chee Chan, Shatin (CN); Rossa Wai Kwun Chiu, Shatin (CN)

(73) Assignee: The Chinese University of Hong Kong, Shatin, New Territories (HK)

( * ) Notice: Subject to any disclaimer, the term of this patent is extended or adjusted under 35 U.S.C. 154(b) by 292 days.

(21) Appl. No.: 15/273,090

(22) Filed: Sep. 22, 2016

(65) Prior Publication Data

US 2017/0081720 A1    Mar. 23, 2017

Related U.S. Application Data

(60) Provisional application No. 62/222,157, filed on Sep. 22, 2015.

(51) Int. Cl.
  *G06F 19/00* (2018.01)
  *C12Q 1/6883* (2018.01)

(52) U.S. Cl.
  CPC ..... *C12Q 1/6883* (2013.01); *C12Q 2600/156* (2013.01)

(58) Field of Classification Search
  CPC ............ C12Q 1/6827; C12Q 2537/165; C12Q 1/6869; C12Q 2535/122; C12Q 2537/16;
  (Continued)

(56) References Cited

U.S. PATENT DOCUMENTS 8,467,976 B2    6/2013  Lo et al.
2012/0010085 A1*  1/2012  Rava .................. C12Q 1/6827
                                              506/2

(Continued)

FOREIGN PATENT DOCUMENTS

CN    104254618 A    12/2014
WO    2014/043763 A1    3/2014

OTHER PUBLICATIONS

International Search Report and Written Opinion dated Dec. 29, 2016 in PCT Application No. PCT/CN2016/099682; 8 pages.
(Continued)

*Primary Examiner* — Mary K Zeman
(74) *Attorney, Agent, or Firm* — Kilpatrick Townsend & Stockton LLP

(57) ABSTRACT

Embodiments of the present invention provide methods, systems, and apparatus for deducing the fetal DNA fraction in maternal plasma without using paternal or fetal genotypes. Maternal genotype information may be obtained from a maternal-only DNA sample or may be assumed from shallow-depth sequencing of a biological sample having both maternal and fetal DNA molecules. Because sequencing may be at shallow depths, a locus may have only few reads and may fail to exhibit a non-maternal allele even if a non-maternal allele is present. However, normalized parameters that characterize non-maternal alleles sequenced can be used to provide an accurate estimate of the fetal DNA fraction, even if the amount of non-maternal alleles is in error. Methods described herein may not need high-depth sequencing or enrichment of specific regions. As a result, these methods can be integrated into widely used non-invasive prenatal testing and other diagnostics.

45 Claims, 19 Drawing Sheets

(58) Field of Classification Search
CPC ............ C12Q 1/6883; C12Q 2600/156; C12Q
1/6809; C12Q 1/6874; C12Q 2600/172;
C12Q 1/6858; C12Q 1/6876; C12Q
2545/113; C12Q 1/68; C12Q 2525/204;
C12Q 2545/101; C12Q 1/6879; C12Q
1/6806; C12Q 2537/143; C12Q 2545/114;
C12Q 1/686; C12Q 1/6881; C12Q
1/6844; C12Q 2535/125; C12Q 2539/10;
G06F 19/18; G06F 19/22; G06F 19/24;
G06F 19/00; G06F 19/20; G06F 19/12;
G06F 19/34; G06F 19/16; G06F 19/26;
G06F 19/14; G06F 19/28; G16H 50/20;
G16H 10/40; G16H 50/30; G06N 7/005;
G06N 99/005; G06N 20/00; C12N 15/11;
G01N 2570/00; G01N 2800/387; G01N
33/00; G01N 33/48; G01N 2800/368;
G01N 2800/385; G01N 33/5308; G01N
33/6893; G01N 33/5023; G01N
33/56966; G16B 20/00; G16B 30/00;
G16B 40/00; G16B 25/00; G16B 5/00;
G16B 15/00; G16B 45/00; G16B 10/00;
G16B 30/10; G16B 20/10; G16B 20/20;
G16B 35/00; G16B 40/20; G16B 40/30;
G16B 50/00; C12P 19/34
See application file for complete search history.

(56) References Cited

U.S. PATENT DOCUMENTS

| 2012/0264121 | A1* | 10/2012 | Rava | C12O 1/6809 435/6.11 |
| 2013/0237431 | A1 | 9/2013 | Lo et al. | |
| 2014/0065621 | A1* | 3/2014 | Mhatre | C12Q 1/6883 435/6.12 |
| 2015/0004601 | A1* | 1/2015 | Struble | C12O 1/6879 435/6.11 |
| 2016/0017412 | A1* | 1/2016 | Srinivasan | C12O 1/6869 506/2 |
| 2016/0217251 | A1 | 7/2016 | Lo et al. | |
| 2016/0244838 | A1* | 8/2016 | Babiarz | C12Q 1/6883 |
| 2017/0314073 | A1* | 11/2017 | Gromminger | C12Q 1/6827 |

OTHER PUBLICATIONS

Kim, Sung K. et al.; "Determination of fetal DNA fraction from the plasma of pregnant women using sequence read counts"; Prenatal Diagnosis; 2015; vol. 35; pp. 810-815.

Lun, Fiona M.F. et al.; "Noninvasive prenatal diagnosis of monogenic diseases by digital size selection and relative mutation dosage on DNA in maternal plasma"; PNAS; Dec. 16, 2008; vol. 105, No. 50; pp. 19920-19925.

* cited by examiner

800 ↘

802 — Biological Sample(s)

804 — Obtain sequencing reads from DNA molecules

806 — Obtain first data set of sequenced reads

808 — Obtain second data set of sequenced reads

810 — Identify an exclusive allele in each locus of first set of loci

816 — Identify second set of loci that exhibits an alternative allele

820 — Determine first amount of loci

822 — Determine second amount of loci in second set of loci

Locus: a, b, c, d, e, f, g, h, i

814 · 812 · 818

824 — Determine apparent allelic discrepancy (AAD) from first amount and second amount, e.g.
$$AAD = \frac{Second\ amount}{First\ amount} \times 100\%$$

826 — Analyzing biological sample using AAD

828 — Fetal DNA fraction (%) vs AAD

*FIG. 8*

|  | Size-based fetal DNA fraction (%) | AAD-based fetal DNA fraction (%) | Absolute Difference |
|---|---|---|---|
| Monozygotic twins | 13 | 14 | 1 |
| Monozygotic twins | 9 | 8 | 1 |
| Monozygotic twins | 17 | 19 | 2 |
| Dizygotic twins | 10 | 18 | 8 |
| Dizygotic twins | 15 | 19 | 4 |
| Dizygotic twins | 10 | 15 | 5 |

*FIG. 14*

ACCURATE DEDUCTION OF FETAL DNA FRACTION WITH SHALLOW-DEPTH SEQUENCING OF MATERNAL PLASMA

CROSS-REFERENCES TO RELATED APPLICATIONS

This application claims the benefit of priority to U.S. Application 62/222,157, filed Sep. 22, 2015, the contents of which are incorporated herein by reference for all purposes.

BACKGROUND

The discovery of circulating cell-free fetal DNA in maternal plasma [Lo Y M et al. (1997), Lancet, 350: 485-487] has catalyzed a series of new avenues for non-invasive prenatal diagnosis, including fetal RhD blood group genotyping [Lo Y M et al. (1998), N Engl J Med, 339: 1734-1738, Finning K et al. (2008), BMJ, 336: 816-818], fetal sex determination for sex-linked disorders [Costa J M, Benachi A, Gautier E (2002), N Engl J Med, 346: 1502], chromosomal aneuploidy detection [Lo Y M et al. (2007), Proc Natl Acad Sci USA. 104: 13116-13121; Chiu R W et al. (2008), Proc Natl Acad Sci USA 105: 20458-20463; Chiu R W, Cantor C R, Lo Y M (2009), Trends Genet, 25: 324-331; Fan H C et al. (2008), Proc Natl Acad Sci USA, 105: 16266-16271; Chiu R W et al. (2011), BMJ 342: c7401; Yu S C et al. (2014), Proc Natl Acad Sci USA, 111: 8583-8588], and detection of monogenic diseases [Lo Y M D et al. (2010), Sci Transl Med, 2: 61ra91; Lam K W et al. (2012), Clin Chem.; New M I et al. (2014), The Journal of Clinical Endocrinology & Metabolism, 99: E1022-E1030; Yoo S-K et al. (2015), Clinical Chemistry; Ma D et al. (2014), Gene, 544: 252-258; Tsui N B et al. (2011), Blood, 117: 3684-3691].

Among the aforementioned applications, accurate deduction of the fetal DNA fraction (also known as fractional fetal DNA concentration or fetal DNA percentage) is important for accurate statistical interpretations of the results of non-invasive prenatal diagnosis through the use of plasma DNA, especially when the statistics models dependent on this parameter are used in the detection of chromosomal aneuploidies [Sparks A B et al., (2012), Am J Obstet Gynecol, 206: 319 e311-319 and the determination of monogenic disease inheritance [Lo Y M et al. (2007), Proc Natl Acad Sci USA. 104: 13116-13121; Lo Y M D et al. (2010), Sci Trans/Med, 2: 61ra91; Lam K W et al. (2012), Clin Chem.; New M I et al. (2014), The Journal of Clinical Endocrinology & Metabolism, 99: E1022-E1030; Yoo S-K et al. (2015), Clinical Chemistry; Tsui N B et al. (2011), Blood, 117: 3684-3691]. For instance, the fetal DNA fraction is a central parameter in Relative Haplotype Dosage Analysis (RHDO) used to accurately determine which maternal haplotype was transmitted to fetus [Lo Y M D et al. (2010), Sci Transl Med, 2: 61ra91; Lam K W et al. (2012), Clin Chem.; New M I et al. (2014), The Journal of Clinical Endocrinology & Metabolism, 99: E1022-E1030]. In this diagnostic approach, the underlying principle is that the relative dosage of the maternal haplotype transmitted to the fetus will be slightly over-represented than the untransmitted one and the fetal DNA fraction is used to determine statistical significance of the over-representation.

To date, there are already many methods developed to estimate the fractional fetal DNA concentration in the maternal plasma of a pregnant woman. For example, the specific signal originating from Y chromosome is used to deduce the fetal DNA fractions in pregnancies carrying male fetuses [Chiu R W et al. (2011), BMJ 342: c7401; Lo Y M et al. (1998), Am J Hum Genet, 62: 768-775; Lun F M et al. (2008), Clin Chem 54: 1664-1672; Hudecova I et al. (2014), Plos One, 9: e88484]. However, the Y chromosome specific signal based approaches are not applicable for pregnancies carrying female fetuses. An alternative approach is to use single nucleotide polymorphism (SNP), such that the ratio of the fetal specific alleles to the shared alleles is calculated to infer the fetal DNA fraction. In this approach, genotype information has to be known and should fit one of following situations: (a) the mother is homozygous while the fetus is heterozygous; (b) both paternal and maternal genotypes are homozygous but with different alleles [Lo Y M D et al. (2010), Sci Transl Med, 2: 61ra91; Liao G J et al. (2011), Clin Chem, 57: 92-101. However, on one hand, in the actual clinical scenarios during non-invasive prenatal diagnosis, the fetal genotypes are not available beforehand. On the other hand, the prevalence of paternal discrepancy can be as high as 30%, suggested by an epidemiological study on paternal discrepancy around the world [Bellis M A, Hughes K, Hughes S, Ashton J R (2005) J Epidemiol Community Health, 59: 749-754], which limits the availability of the paternal DNA for data analysis. Even though a parental-genotype-independent algorithm was developed to obviate the prerequisite of extra genotype information by utilizing the high-depth sequencing of maternal plasma DNA (for example targeted sequencing of maternal plasma DNA) across different SNP sites [Jiang P et al. (2012), Bioinformatics, 28: 2883-2890], additional effort is required to capture a set of regions of interest, for example, through the use of hybridization- or amplicon-based enrichment systems [Sparks A B et al., (2012), Am J Obstet Gynecol, 206: 319 e311-319; Liao G J et al. (2011), Clin Chem, 57: 92-101].

In addition to SNP dependent approaches, SNP-independent methods are also being explored. For example, fragment sizes of maternal plasma DNA can be used for estimating fetal DNA fraction [Yu S C et al. (2014), Proc Natl Acad Sci USA, 111: 8583-8588; Kim S K et al. (2015), Prenatal diagnosis: n/a-n/a] because the fetal-derived DNA are generally shorter than maternal-derived DNA [Lo Y M D et al. (2010), Sci Transl Med, 2: 61ra91]. However, some other conditions will influence the accuracy of the size-based fetal DNA fraction estimation, for example, systemic lupus erythematosus [Chan R W et al. (2014), Proc Natl Acad Sci USA, 111: E5302-5311]. As an alternative, fetal-specific epigenetic changes, such as methylated RASSF1A and unmethylated SERPINB5 sequences, were demonstrated to be fetal markers for fetal DNA fraction prediction irrespective of genotype information [Chan K C et al. (2006), Clin Chem, 52: 2211-2218; Chim S S et al. (2005), Proc Natl Acad Sci USA, 102: 14753-14758]. However, the analytical procedures for quantifying these epigenetic markers involve either bisulfite conversion or digestion with methylation-sensitive restriction enzymes, and may thus potentially affect the precision of these methods.

Accordingly, it is desirable for new techniques to provide fetal DNA fraction information from maternal plasma.

BRIEF SUMMARY

Embodiments of the present invention provide methods, systems, and apparatus for deducing the fetal DNA fraction in maternal plasma. The fetal DNA fraction can be determined without specifically determining paternal or fetal genotypes. A separate parameter may be determined, and a calibration curve can be used to determine the actual fetal DNA fraction. For example, a ratio can be determined of an amount of reads having an allele nominally identified as a non-maternal allele and an amount of reads having an allele nominally identified as a maternal allele. As another example, a ratio can be determined of an amount of loci exhibiting a nominal non-maternal allele and an amount of homozygous maternal loci, as determined from a separate dataset. A difference in size of reads may also be used. The loci (sites) may be limited to known heterozygous loci in a population.

Maternal genotype information may be obtaining from a maternal-only DNA sample or may be assumed from a sequencing (e.g., at shallow-depth) of a biological sample having both maternal and fetal DNA molecules. The actual or assumed maternal genotype information can be combined with sequencing of DNA molecules from the biological sample. Even though it may not be definitively known whether the mother is homozygous at a particular loci or whether the fetus is heterozygous, embodiments can use reads at such sites in determining the separate parameter, which is a difference from previous techniques. Any errors are shown to be consistent, and thus compensate by the calibration curve, which can be generated once using a separate technique to determine the fetal DNA fraction.

Because sequencing may be at shallow depths, a locus may have only few reads and may fail to exhibit a non-maternal allele even if a non-maternal allele is present. However, normalized parameters that characterize non-maternal alleles sequenced can be used to provide an accurate estimate of the fetal DNA fraction, even if the amount of non-maternal alleles at a locus or at all loci is not representative of the fetal DNA fraction. These normalized parameters may include the amount of sequence reads with the non-maternal allele or the amount of loci with the non-maternal allele. Methods described herein may not need high-depth sequencing or enrichment of specific regions. As a result, these methods can be integrated into widely used non-invasive prenatal testing and other diagnostics.

Some embodiments are directed to systems and computer readable media associate with methods described herein.

A better understanding of the nature and advantages of embodiments of the present invention

BRIEF DESCRIPTION OF THE DRAWINGS

FIG. 8 shows an illustration of measuring fetal DNA fraction without obtaining a maternal genotype, a paternal genotype, or a biological sample containing only maternal DNA molecules according to embodiments of the present invention.

FIG. 14 is a table of fetal DNA fractions calculated for six different sets of twins according to embodiments of the present invention.

TERMS

Figure 1:
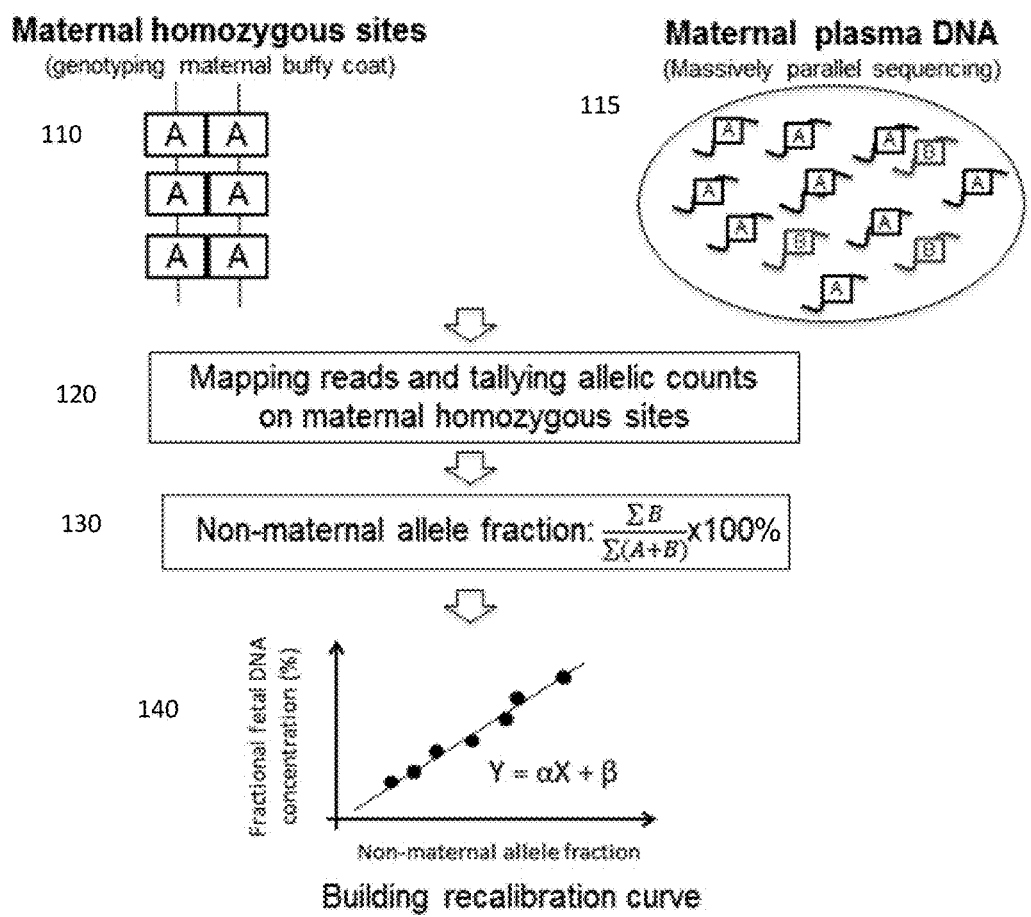
FIG. 1 is a schematic illustration of measuring fractional fetal DNA concentration using a maternal genotype according to embodiments of the present invention.

As used herein, the term "locus" or its plural form "loci" is a location or address of any length of nucleotides (or base pairs) which has a variation across genomes. A "sequence read" refers to a string of nucleotides sequenced from any part or all of a nucleic acid molecule. For example, a sequence read may be a short string of nucleotides (e.g., 20-150) sequenced from a nucleic acid fragment, a short string of nucleotides at one or both ends of a nucleic acid fragment, or the sequencing of the entire nucleic acid fragment that exists in the biological sample. A sequence read may be obtained in a variety of ways, e.g., using sequencing techniques or using probes, e.g., in hybridization arrays or capture probes, or amplification techniques, such as the polymerase chain reaction (PCR) or linear amplification using a single primer or isothermal amplification.

A "biological sample" refers to any sample that is taken from a subject (e.g., a human, such as a pregnant woman, a person with cancer, or a person suspected of having cancer, an organ transplant recipient or a subject suspected of having a disease process involving an organ (e.g., the heart in myocardial infarction, or the brain in stroke, or the hematopoietic system in anemia) and contains one or more nucleic acid molecule(s) of interest. The biological sample can be a bodily fluid, such as blood, plasma, serum, urine, vaginal fluid, fluid from a hydrocele (e.g. of the testis), vaginal flushing fluids, pleural fluid, ascitic fluid, cerebrospinal fluid, saliva, sweat, tears, sputum, bronchoalveolar lavage fluid, discharge fluid from the nipple, aspiration fluid from different parts of the body (e.g. thyroid, breast), etc. Stool samples can also be used. In various embodiments, the majority of DNA in a biological sample that has been enriched for cell-free DNA (e.g., a plasma sample obtained via a centrifugation protocol) can be cell-free, e.g., greater than 50%, 60%, 70%, 80%, 90%, 95%, or 99% of the DNA can be cell-free. The centrifugation protocol can include, for example, 3,000 g×10 minutes, obtaining the fluid part, and re-centrifuging at for example, 30,000 g for another 10 minutes to remove residual cells. The cell-free DNA in a sample can be derived from cells of various tissues, and thus the sample may include a mixture of cell-free DNA.

"Nucleic acid" may refer to deoxyribonucleotides or ribonucleotides and polymers thereof in either single- or double-stranded form. The term may encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs may include, without limitation, phosphorothioates, phosphoramidites, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

The term "nucleotide," in addition to referring to the naturally occurring ribonucleotide or deoxyribonucleotide monomers, may be understood to refer to related structural variants thereof, including derivatives and analogs, that are functionally equivalent with respect to the particular context in which the nucleotide is being used (e.g., hybridization to a complementary base), unless the context clearly indicates otherwise.

A "sequence read" refers to a string of nucleotides sequenced from any part or all of a nucleic acid molecule. For example, a sequence read may be the entire nucleic acid fragment that exists in the biological sample. A sequence read may be obtained from a single-molecule sequencing.

A "classification" refers to any number(s) or other characters(s) that are associated with a particular property of a sample. For example, a "+" symbol (or the word "positive") could signify that a sample is classified as having deletions or amplifications. The classification can be binary (e.g., positive or negative) or have more levels of classification (e.g., a scale from 1 to 10 or 0 to 1). The term "cutoff" and "threshold" refer to a predetermined number used in an operation. For example, a cutoff size can refer to a size above which fragments are excluded. A threshold value may be a value above or below which a particular classification applies. Either of these terms can be used in either of these contexts.

The term "size profile" generally relates to the sizes of DNA fragments in a biological sample. A size profile may be a histogram that provides a distribution of an amount of DNA fragments at a variety of sizes. Various statistical parameters (also referred to as size parameters or just parameter) can be used to distinguish one size profile to another. One parameter is the percentage of DNA fragment of a particular size or range of sizes relative to all DNA fragments or relative to DNA fragments of another size or range.

DETAILED DESCRIPTION

Noninvasive prenatal testing (NIPT) using massively parallel sequencing of maternal plasma DNA is increasingly recognized as an essential component in modern prenatal diagnosis and has been rapidly adopted in clinical use world-wide. To guarantee the precise interpretations of this kind of noninvasive prenatal diagnosis, fetal DNA fraction becomes a crucial parameter to be measured. Although various methods have been developed to estimate this parameter, there is a paucity of generic and broadly-applicable approaches.

Some embodiments allow accurate estimation of the fetal DNA fraction, using actual or assumed maternal genotypes and random massively parallel sequencing of the maternal plasma. The fetal DNA fraction may be related to a parameter characterizing the amount of non-maternal material in the biological sample. The amount of non-maternal material may be calculated as the fraction of sequence reads that are non-maternal, or the proportion of loci that have a non-maternal allele. In either of these calculations, the parameter may not accurately represent the actual fetal DNA fraction. Sequencing may be done at shallow depths, so that not all non-maternal alleles that are present may be sequenced. In addition, the calculation of a non-maternal fraction of sequence reads may include reads at sites without a non-maternal allele. Including these sequence reads in the calculation of non-maternal fraction would then include potentially homozygous sites, which would not normally be used in conventional methods to determine the fetal DNA fraction. Similarly, calculating the proportion of loci that have a non-maternal allele may include using a number of potentially homozygous loci, which are normally not considered important in conventional methods of calculating fetal DNA fraction.

The fetal DNA fraction, however, is found to be related to the fraction of non-maternal alleles originating from maternal homozygous loci in the plasma of pregnant women, even when the fraction of non-maternal alleles does not accurately account for all non-maternal alleles. In addition, the fetal DNA fraction is found to be correlated with the proportion of loci that have a non-maternal allele, even when the sequence reads do not reveal all loci with non-maternal alleles. These methods were validated with experimental data. Using shallow-depth sequencing, methods can be more efficient and economical than conventional methods. In addition, these methods do not depend on a paternal genotype or specific genetic traits in the fetus, and therefore the methods can be applied broadly to any pregnant female. These methods can also further enhance the clinical interpretations of noninvasive prenatal testing.

I. Analyzing DNA using Amount of Sequence Reads

Maternal-only DNA can be sequenced and compared to DNA in a sample containing both maternal DNA and fetal DNA in order to estimate the fetal DNA fraction. The maternal-only DNA may be sequenced to identify homozygous sites. A sample containing a mixture of maternal DNA and fetal DNA (e.g., maternal plasma or serum) may then be sequenced. In mixture, some of the identified homozygous sites may have a sequence read of a non-maternal allele while other identified homozygous sites may have sequence reads of only alleles identical to the maternal allele. These reads of non-maternal alleles and alleles identical to the maternal alleles can be used to calculate a non-maternal fraction. This non-maternal fraction, which may include in the denominator the sites that have only alleles identical to the maternal allele, may not equal the actual fetal DNA fraction. However, this non-maternal fraction may be related to the fetal DNA fraction. A higher fetal DNA fraction may result in a higher non-maternal fraction. A calibration curve of the fetal DNA fraction and the non-maternal fraction can be used to relate an estimate of the fetal DNA fraction to the non-maternal fraction calculated for the sample.

The sample containing both maternal DNA and fetal DNA, however, may be sequenced at shallow depth, with a locus possibly having only one or two reads. Even if the reads in the sample of both maternal DNA and fetal DNA show the same alleles as the maternal alleles, the site cannot be determined with high statistical confidence to be homozygous in the fetus because a fetal non-maternal allele may have been present but just not exhibited in the few reads. Shallow depth sequencing may then underestimate the actual number of non-maternal alleles in the fetal DNA.

Even though the fraction of non-maternal alleles may not be the actual fraction of non-maternal alleles, this fraction can be used with a calibration curve to obtain an accurate fetal DNA fraction. The fetal DNA fraction is found to be related to the non-maternal fraction, even if the fraction is underestimated or otherwise does not include an accurate count of non-maternal alleles. A higher fetal DNA fraction increases the likelihood of non-maternal alleles being sequenced, thereby increasing the non-maternal fraction. As a result, even at shallow depths, the relationship between the non-maternal fraction and the fetal DNA fraction can be represented in a calibration curve and used to estimate fetal DNA fraction.

A. Non-Maternal Fraction and Calibration Curve

The non-maternal fraction of the sample containing maternal DNA and fetal DNA is a ratio of a first amount of reads with a non-maternal allele and a second amount of reads. Both amounts of reads may be at certain sites in the maternal genome, including sites that are known to have a high likelihood of heterozygosity (i.e., sites with SNPs). The second amount of reads may include the reads from the sample of the DNA mixture that have the maternal allele. In some embodiments, the second amount may be a total amount of reads at the sites, where the total amount is the sum of the first amount and the reads with the maternal allele.

This non-maternal fraction may not equal the actual fraction of non-maternal alleles present in a biological sample. Instead, the non-maternal fraction reflects the sequenced reads that are non-maternal alleles in the maternal plasma. Thus, the non-maternal fraction may depend on sequencing errors, genotyping errors, the underlying number of sites where mother is homozygous and fetus is heterozygous (informative SNP sites), and the fetal DNA fraction. Results show that the sequencing errors, the genotyping errors, and the underlying number of informative sites are relatively constant. Thus, the fetal DNA fraction can be determined from the non-maternal allele fraction.

FIG. 1 shows a use of the non-maternal fraction to determine the fractional fetal DNA. Homozygous sites are identified in the maternal DNA. Maternal plasma is sequenced and reads of alleles are counted at the identified homozygous sties. The non-maternal fraction is calculated from the sum of the reads of the alleles at these sites, even if no non-maternal alleles are sequenced at some of the sites. The resulting non-maternal fraction can then be compared to a calibration curve of previously measured fractional fetal DNA concentrations and previously calculated non-maternal fractions. An estimated fractional fetal DNA concentration may be obtained.

At section 110, the maternal genotype is obtained from maternal tissues, for example, by analyzing buffy coat or buccal swab samples using microarray-based genotyping technologies. In other embodiments, the maternal genotype analysis may also be performed using a sample comprising a mixture of fetal and maternal DNA.

Section 110 shows homozygous sites in the maternal genotype. Each site has two A alleles, illustrated as boxes. The A allele may or may not be the result of a SNP with an A nucleotide. Although section 110 shows no heterozygous sites in the maternal genome, heterozygous sites may be between homozygous sites. The homozygous sites may be limited to only sites that are known to have a single nucleotide polymorphism (SNP), which may be identified in a database such as dbSNP or HapMap. The maternal sites that appear homozygous can be identified from the genotyping information and aligning to a reference genome. The genotyping may be performed using any suitable genotyping technique, e.g., using sequencing (which may include alignment to a reference genome), targeted sequencing, amplicon-based sequencing, mass spectrometry, droplet digital PCR, hybridization array, or microarray.

The number of homozygous sites used can depend on the microarray platform used. For example, for Affymetrix, there are ~700,000 homozygous sites and for BeadChip there are ~2 million. Thus, there are sufficient sites for embodiments to focus on SNP sites rather than any site in the entire genome, although the latter is possible.

At section 115, maternal plasma DNA is sequenced. The maternal plasma includes many DNA fragments, which may include alleles from the identified homozygous sites. Section 115 shows fragments with the A allele, the maternal allele present in the homozygous sites, and fragments with a B allele, a non-maternal allele not present in the homozygous sites. The maternal plasma DNA may be sequenced with massively parallel sequencing. The maternal plasma DNA may be sequenced at shallow depths. For example the number of sequencing reads may be less than 0.1×, 0.2×, 0.3×, 0.4×, 0.5×, 0.8×, 1×, 1.5×, 2×, 3×, 4×, 5×, and 10× coverage of a haploid human genome. The number of reads may be less than or equal to 50 million reads, including less than or equal to 30 million reads, 20 million reads, 15 million reads, less than or equal to 10 million reads, less than or equal to 8 million reads, less than or equal to 5 million reads, less than or equal to 4 million reads, less than or equal to 2 million reads, or less than or equal to 1 million reads. The sequence reads obtained in section 110 may also be determined at a shallow depth. Accordingly, the genotype of homozygous may not be accurate (i.e., the female could have a B at one of the sites identified as homozygous), but results show that such inaccuracies are consistent across samples, thereby allowing a calibration curve to provide the fetal DNA fraction with a desired accuracy.

At section 120, the sequence reads from the maternal plasma (or other sample having a mixture of maternal and fetal DNA) are mapped to a reference genome. The mapping may be made only to the homozygous sites identified in the maternal genome. The alignment with the homozygous sites distinguishes the B non-maternal alleles, which would typically be from a paternal contribution, but can relate to sequencing error, de novo mutations, and other examples mentioned herein. The B allele could also be from the mother in instances where the genotyping at section 110 is done at a shallow depth, as described above.

The sequence reads from the maternal plasma are then totaled for both the A maternal allele and the B non-maternal allele. Sequence reads with a B non-maternal allele at the identified homozygous sites are totaled. Sequence reads with an A maternal allele at the identified homozygous sites are totaled, even if no B non-maternal allele is sequenced at the particular site.

At section 130, the non-maternal allele fraction is determined. To calculate the non-maternal allele fraction, the total number of the sequence reads with the B non-maternal allele at the homozygous sites, $\Sigma B$, is obtained from the reads in section 120. The total number of sequence reads with either the B non-maternal allele or the A maternal allele, $\Sigma(A+B)$, is obtained from the reads in section 120. The non-maternal allele fraction is calculated as the ratio of the total number of sequence reads with the B non-maternal allele over the total number of sequence reads with either the A maternal allele or the B non-maternal allele, and the ratio is converted to a percentage:

$$\frac{\Sigma B}{\Sigma(A+B)} \times 100. \quad (1)$$

Other related fractions or percentages may be used. For example, the total number of sequence reads with the B non-maternal allele may be divided by the sum of the total number of sequence reads with only the A maternal allele. Reciprocals of any fraction described herein may also be used.

In practice, the fraction of non-maternal alleles is governed by the fetal DNA fraction, as well as the sequencing and genotyping errors. Provided that the errors stemming from genotyping and sequencing platforms are systemic errors that are relatively constant under a certain circumstance, the fractional fetal DNA concentration is proportional to the fraction of non-maternal alleles measured in maternal plasma. The fetal DNA fraction can be predicted by analyzing the fraction of non-maternal alleles.

At section 140, a calibration curve is shown for obtaining the fractional fetal DNA concentration from the non-maternal allele fraction. The calibration curve can have various functional forms, e.g., linear, quadratic, or any polynomial. Section 140 shows a linear calibration curve, with X as the non-maternal fraction, calculated from Equation (1), Y as the fractional fetal DNA concentration, a as the slope of the line, and β as the y-intercept of the line.

To establish the calibration curve, embodiments can use a series of samples with known fetal DNA fractions (e.g., estimated from Y chromosome, based on informative SNP sites, etc.). For each of the samples with known fetal DNA fractions, the non-maternal allele fraction is measured. A functional fit of the known fetal DNA fraction values to the measured non-maternal fraction can be determined and used as the calibration curve. These samples may be termed calibration samples.

In various embodiments, the calibration value(s) can correspond to the calibration value(s) of the calibration data point(s) determined from the calibration sample(s) or any calibration values determined therefrom, e.g., of a calibration function that approximates the calibration data points. The one or more calibration samples may or may not include any additional sample used to determine the preferred ending sites.

For each of the one or more calibration samples, a corresponding proportional contribution of the first tissue type can be measured, e.g., using a tissue-specific allele. A corresponding relative abundance can be determined using the corresponding numbers of cell-free DNA molecules ending within the plurality of windows corresponding to the first set of genomic positions. The measured proportional contribution and relative abundance can provide a calibration data point. The one or more calibration data points can be a plurality of calibration data points that form a calibration function that approximates the plurality of calibration data points. Further details of use of calibration values can be found in U.S. Patent Publication 2013/0237431.

In determining the non-maternal allele fraction, every read with a non-maternal allele at a site can be counted, even if is not known whether the fetus truly has the non-maternal allele or whether it is an error. In some implementations, no minimum number of non-maternal alleles may be required before a site is used, which would otherwise be used as a test to determine that the allele is not an error. In addition, sites that do not have a sequence read of a non-maternal allele may still be used in the determination of the non-maternal allele fraction. For example, even if some of the sites in the maternal plasma DNA have only sequence reads of the maternal allele, these reads of the maternal allele may still appear in the denominator for the calculation of the non-maternal allele fraction in Equation (1). The resulting non-maternal allele fraction may then not reflect the actual non-maternal allele fraction because the calculation includes a site that may not have a non-maternal allele.

To ensure greater accuracy, embodiments can filter out the reads carrying an allele for a site that is not annotated in dbSNP database, e.g., assuming all SNPs used are biallelic. For example, a SNP site is annotated as A/C in dbSNP database. A read carrying "G" seen in plasma will be filtered out, but the site can still be used as a reference for other reads being analyzed. This can reduce the sequencing error influence. Further, all reads at site that is not annotated as a SNP site can be filtered out.

B. Training and Validation of Calibration Curves

Maternal plasma samples were used to validate the use of the non-maternal allele fraction in estimating the fetal DNA fraction. Some of the samples were used to as training data sets, in order to generate calibration curves of the actual fetal DNA fraction versus non-maternal allele fraction. For the remaining samples, the non-maternal allele fraction is determined for each sample, and then the fetal DNA fraction was estimated based on the calibration curve generated from the initial samples. The estimated fetal DNA fractions for the remaining samples are then compared to the actual fetal DNA fractions to verify the accuracy of using the non-maternal allele fraction.

1. Data Sets

Two data sets were used to test the hypothesis as to whether the fetal DNA concentration can be determined from the fraction of non-maternal alleles measured in maternal plasma. For the first data set, there were a total of 35 samples that were genotyped on Affymetrix genotyping microarray (Affymetrix Genome-Wide Human SNP Array 6.0 system) and sequenced with 36 cycles of paired-end mode on Genome Analyzer IIx (Ilumina) as described in [Lo Y M D et al. (2010), Sci Transl Med, 2: 61ra91] and [Yu S C et al. (2014), Proc Natl Acad Sci USA, 111: 8583-8588], respectively. On average, 671,206 (range 635,378-682,501) homozygous sites were obtained among 906,600 SNPs being interrogated on Affymetrix genotyping platform. Meanwhile, after paired-end sequencing reads were mapped to reference human genome using SOPA2 [Yu S C et al. (2014), Proc Natl Acad Sci USA, 111: 8583-8588; Li R Q et al. (2009), Bioinformatics, 25: 1966-1967], a median of Ser. No. 12,961,498 (range 7,728,645-23,454,296) alignable and nonduplicated reads for the samples for subsequent analysis was obtained. The median of almost 13 million reads corresponds to approximately 0.3× coverage.

The second data set had a higher number of reads and number of samples than the first data set. For the second data set, there were a total of 70 samples that were genotyped on BeadChip array (Illumina) and sequenced on HiSeq 2000 sequencer (Illumina) (50 bp×2) [Stephanie C et al. (2013), Clinical Chemistry]. On average, 1,940,577 (range 1,925,282-1,949,532) homozygous loci were obtained among 2,351,072 SNPs being interrogated on BeadChip array (Illumina). After alignment, a median of 69,959,574 (range 26,036,386-94,089,417) alignable and nonduplicated reads were obtained for the samples. The almost 70 million reads corresponds to a coverage of about 2.3×. To evaluate the performance of the fetal DNA fraction prediction, the estimated fetal fraction was compared with the fetal DNA fraction that was determined through the use of the fetus's genotypes as the standard (termed the actual fetal DNA fraction).

2. Non-Maternal Allele Fraction Calculation

The non-maternal allele fraction for each sample is calculated using Equation (1). For the homozygous sites identified from genotyping a maternal-only sample, the number of reads from the corresponding maternal plasma sample is counted. The sum of the number of reads with a non-maternal allele at the identified homozygous sites is divided by the total number of reads at the homozygous sites (i.e., reads with either a non-maternal allele or maternal allele) and then converted to a percentage.

3. Fractional Fetal DNA Concentration Estimation

To confirm that the fractional fetal DNA concentration is proportional to the fraction of non-maternal alleles in maternal plasma, each data set was randomly divided, with some samples in a training set and the remaining samples in an independent validation set. A linear regression was used to model the relationship between the actual fetal DNA fraction (dependent variable Y) and the fraction of non-maternal alleles (independent variable X, calculated by Equation (1)) in maternal plasma by analyzing 12 and 23 samples in the training set of the first data set and second data set, respectively. The actual fetal DNA fraction (F) was deduced by analyzing the reads overlapping with SNPs where the mother was homozygous and the fetus was heterozygous according to the following formula [Lo Y M D et al. (2010), Sci Transl Med, 2: 61ra91].

$$F = \frac{p}{p+q} \quad (2)$$

where p is the number of sequenced reads of the fetal-specific allele and q is the read count of the shared allele. Equation (2) differs from Equation (1) because Equation (2) includes reads from only sites where the mother is homozygous and the fetus is heterozygous, while Equation (1) may also include reads from sites where both the mother and the fetus appear homozygous. In other embodiments, F can be scaled to by 2 to correspond to the total fetal fraction for all fetal DNA. Other ratios can also be used, e.g., p/q.

Accordingly, F is assumed to be the actual fetal DNA fraction and is estimated from sites where the mother is homozygous and fetus is heterozygous. The heterozygosity can be determined by genotyping the placental tissues at the corresponding sites. The samples for which the actual fetal DNA fraction was determined were used to show that the deduced F using embodiments of the present invention are accurate.

4. Results

Figure 2B:
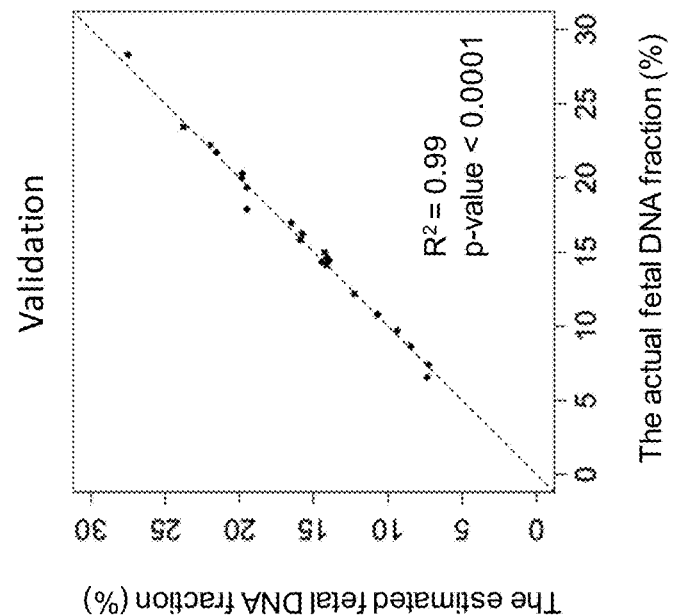
FIG. 2B shows a validation of the regression model in FIG. 2A using an independent data set according to embodiments of the present invention.
Figure 2A:
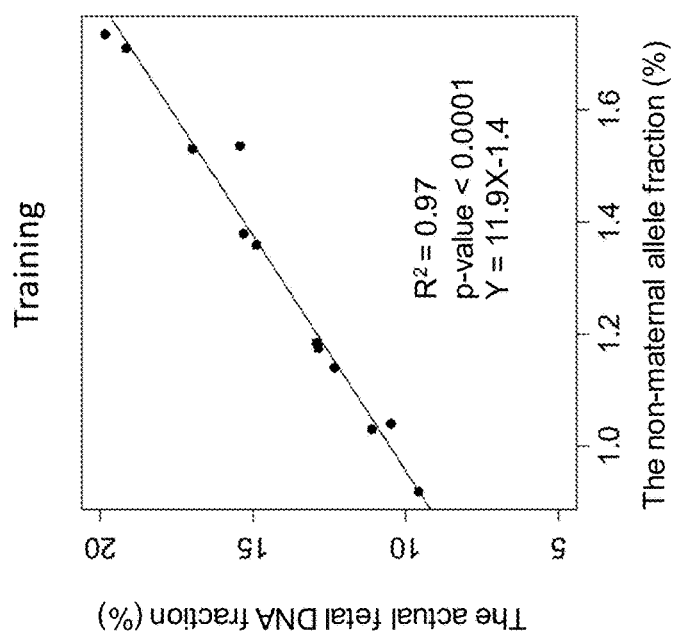
FIG. 2A shows a linear regression model of the actual fetal DNA fraction and the non-maternal allele fraction constructed from a training data set from a first data set according to embodiments of the present invention.

FIG. 2A shows a linear model (Y=11.9X−1.4) constructed using the training data set of the first data set. The actual fetal DNA fraction determined using a previously obtained fetal genotype is shown on the y-axis, and the non-maternal allele fraction is shown on the x-axis. The adjusted R squared was 0.97 (p-value<0.0001).

FIG. 2B shows that the estimated fetal DNA fractions are highly similar to the actual fetal DNA fractions in the first data set. The estimated fetal DNA fraction, using the linear model from FIG. 2A, is shown on the y-axis. The actual fetal DNA fraction determined using a previously obtained fetal genotype is shown on the y-axis. A linear regression is fit to the data, with the resulting fit having an adjusted R squared at 0.99 (p-value<0.0001).

Figures 3A, 3B:
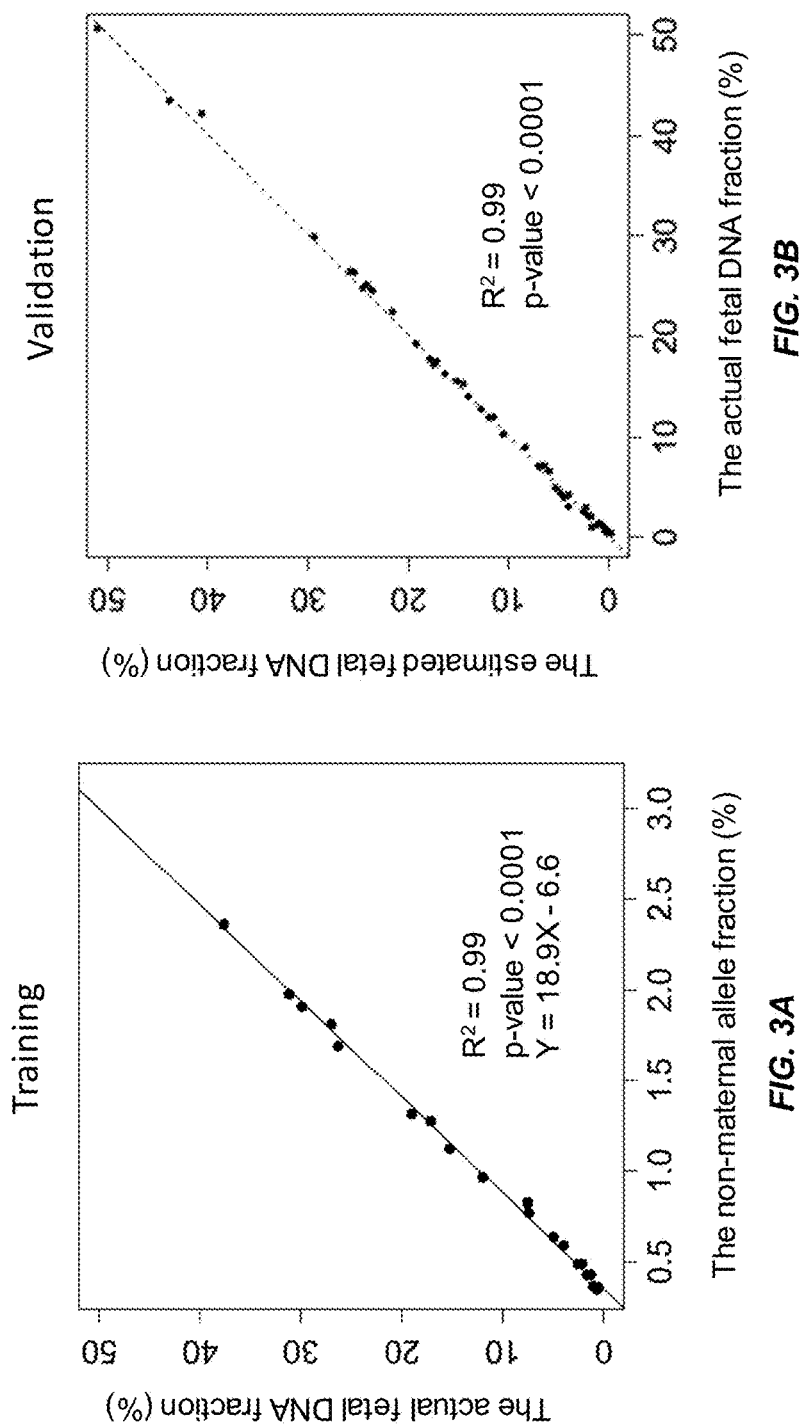
FIG. 3A shows a linear regression model of the actual fetal DNA fraction and the non-maternal allele fraction constructed from a training data set from a second data set according to embodiments of the present invention.
FIG. 3B shows a validation of the regression model in FIG. 3A using an independent data set according to embodiments of the present invention.

FIG. 3A shows a linear model (Y=18.9X−6.6, adjusted R squared of 0.99 and p-value<0.0001) was constructed from 24 samples in the training set of the second data set. The actual fetal DNA fraction determined using a previously obtained fetal genotype is shown on the y-axis, and the non-maternal allele fraction is shown on the x-axis.

FIG. 3B shows that the estimated fetal DNA fractions are highly similar to the actual fetal DNA fractions in the second data set. The estimated fetal DNA fraction, using the linear model from FIG. 2B, is shown on the y-axis. The actual fetal DNA fraction determined using a previously obtained fetal genotype is shown on the y-axis. A linear regression is fit to the data, with the resulting linear fit having an adjusted R squared of 0.99 (p-value<0.0001).

The validation sets in FIG. 2B and FIG. 3B show that the estimated fetal DNA fraction based on calibration curves of the non-maternal allele fraction and the actual fetal DNA fraction are highly correlated to the actual fetal DNA fraction. The linear fits for the validation sets in FIG. 2B and FIG. 3B both have an R squared of 0.99 (p-value<0.0001). A high R squared value indicates that the technique is precise. The points in FIG. 2B and FIG. 3B also lie close to the y=x line, which would indicate a perfect estimation of the actual fetal DNA fraction.

Figure 4A:
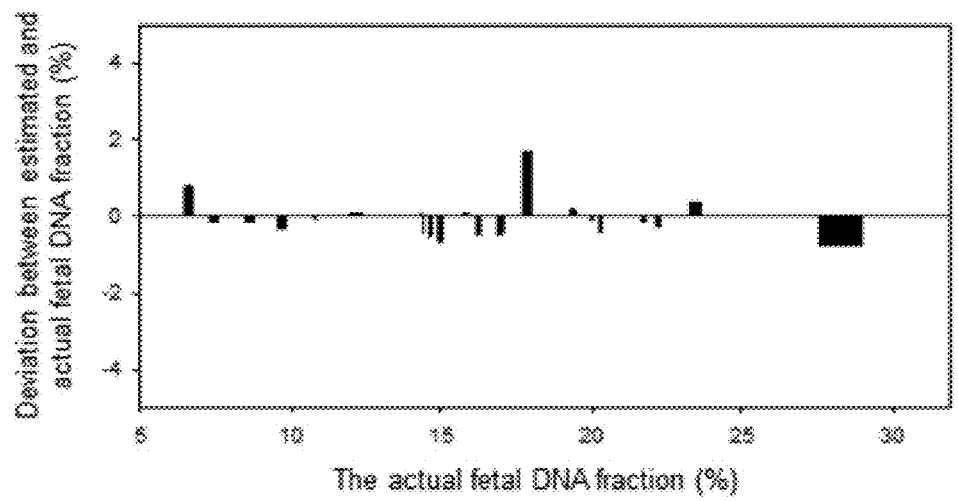
FIG. 4A shows the deviation between the actual fetal DNA fraction and the estimated fetal DNA fraction for the first data set according to embodiments of the present invention.
Figure 4B:
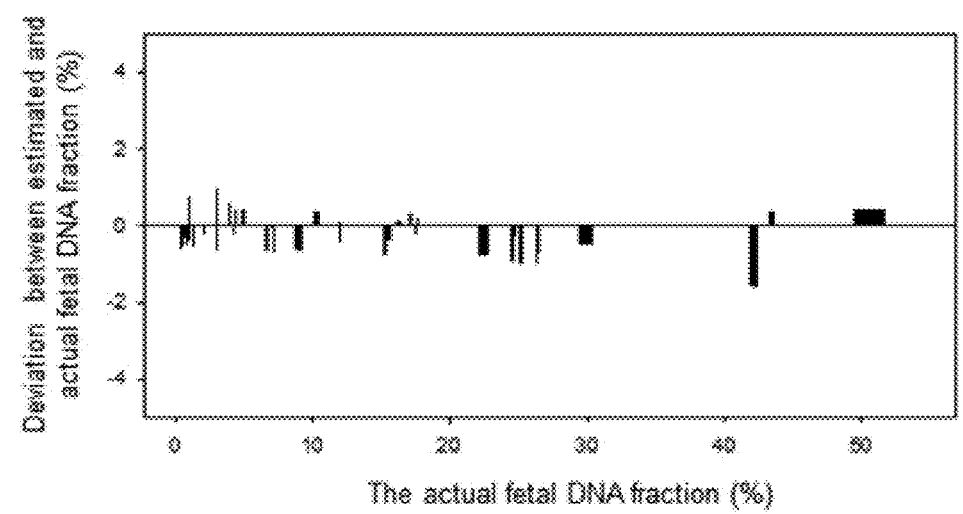
FIG. 4B shows the deviation between the actual fetal DNA fraction and the estimated fetal DNA fraction for the second data set according to embodiments of the present invention.

FIGS. 4A and 4B show the median deviations from the actual fetal DNA fractions. The x-axis in FIG. 4A and FIG. 4B is the actual fetal DNA fraction. The y-axis is the deviation as a percentage between the estimated fetal DNA fraction and the actual DNA fraction for each sample in the validation data sets. A positive value on the y-axis corresponds to the estimated fetal DNA fraction being larger than the actual fetal DNA fraction. A negative value on the y-axis corresponds to the estimated fetal DNA fraction being smaller than the actual fetal DNA fraction. FIG. 4A shows that for the validation set of the first data set, the median deviation is −0.14% and ranges from −0.7% to 1.7%. FIG. 4B shows that for the second data set, the median deviation is −0.22% and ranges from −1.5% to 0.98%. The difference in the results for the two calibration curves for the two data sets can be attributed to the different platforms used. FIG. 4A and FIG. 4B demonstrate that a maximum deviation of under 2% and a median deviation of between −0.14% and −0.22% are possible from estimated fetal DNA fractions using non-maternal allele fractions.

A relative prediction error (E %) was further used to measure the accuracy of the model constructed from the validation data sets, which was defined by:

$$E\% = \frac{|\hat{F} - F|}{F} \times 100\% \tag{2}$$

where $\hat{F}$ represents the estimated fractional fetal DNA concentration and F represents the actual fetal DNA concentration. For example, E %=5% suggests that if an actual fetal DNA fraction was 10%, the readout would be between 9.95% and 10.05% (10%±0.05). The means of E % were found to be 1.7% (range: 0.7-2.9%) and 3.8% (range: 1.3-14.9%) for the first data set and second data set, respectively.

The experimental results confirm that the non-maternal allele fraction can be used to accurately and precisely measure fetal DNA fraction. The accuracy and precision of the estimated fetal DNA fraction is within the range often required for NIPT testing.

C. Accuracy of Fetal DNA Fraction Estimation Depends on the Actual Fractional Fetal DNA Concentration The prediction accuracy is dependent on the actual fetal DNA fraction being analyzed, namely. The higher the fetal DNA fraction is, the more accurate the estimation. The second data set was used to investigate the relationship between the actual fetal DNA fraction and the relative prediction error because there were more data points involving the fetal DNA fraction less than 5% (FIG. 3B), which were collected after delivery.

Figure 5:
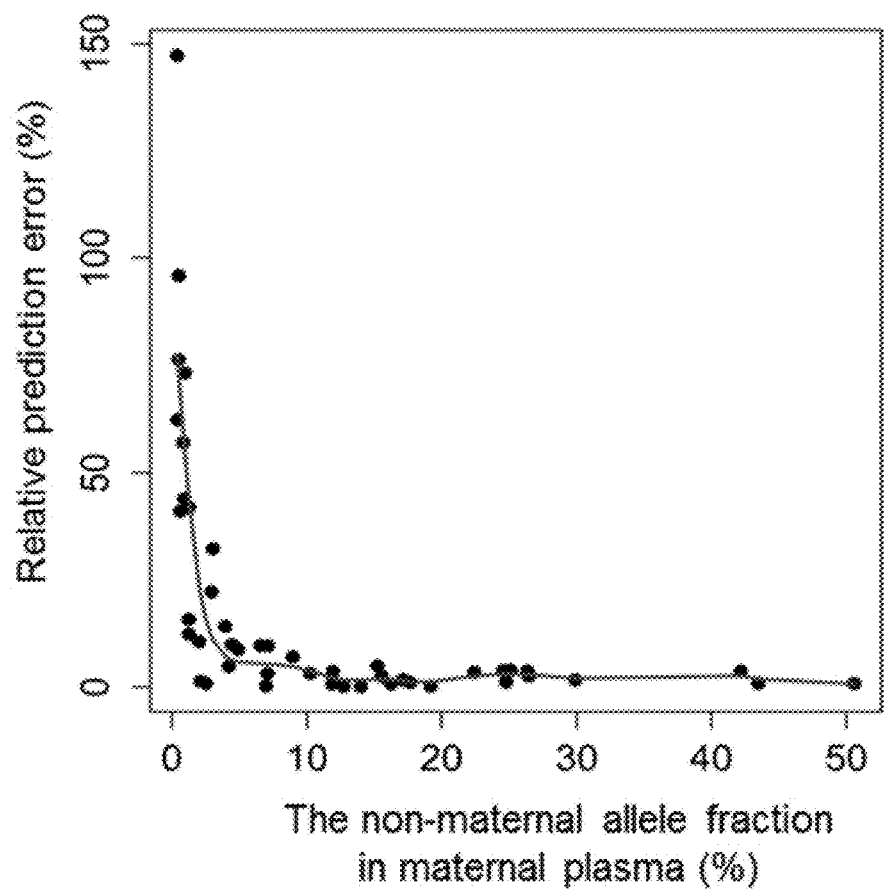
FIG. 5 shows a graph of the relationship between the relative prediction error and the actual fetal DNA fraction according to embodiments of the present invention.

FIG. 5 shows a scatterplot of relative prediction error versus the actual fetal DNA concentration. The relative prediction error in percent is shown on the y-axis, and the non-maternal allele fraction in the maternal plasma is shown as a percent on the x-axis. The scatterplot displays a very clear "L" shape, in which cases with high fetal DNA levels exhibited low prediction errors, and cases with low fetal DNA levels showed relatively high prediction errors. The E % would be close to 5% even for the actual fetal DNA fraction at 5% (FIG. 5).

D. Relationship Between the Sequencing Depth and the Accuracy of Fetal DNA Fraction Estimation To further demonstrate how sequencing depth affects the fetal DNA fraction, a downsampling analysis was performed on the second data set because samples in the second data set have a higher sequencing depth than the first data set, allowing sampling analysis to be conducted multiple times. For each sample of 20 samples, a different number of sequence reads were randomly selected, and paired-end reads were randomly selected from 20 samples in the second data set with 1, 2, 4, 6, and 8 million per sample. The aforementioned analysis of the fetal DNA fraction prediction was repeated. The numbers of sequence reads randomly selected were 1 million, 2 million, 4 million, and 8 million.

Figure 6A:
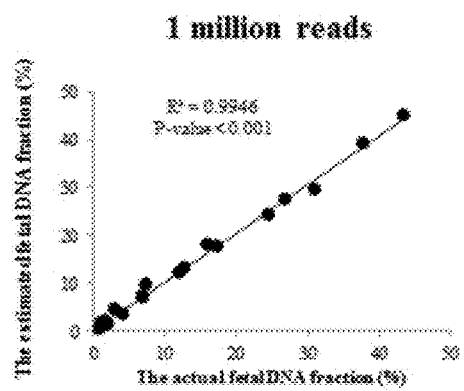
FIGS. 6A, 6B, 6C, and 6D show the accuracies of the fetal DNA fraction prediction at a various sequencing depths according to embodiments of the present invention.

FIG. 6A shows the estimated fetal DNA fraction versus the actual fetal DNA fraction at 1 million reads. A linear regression fit to the data has an R squared of 0.9946 and a p-value less than 0.001.

Figure 6B:
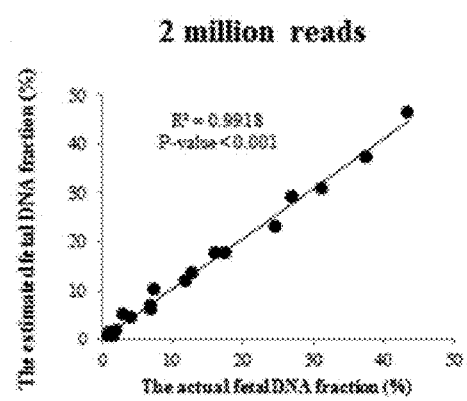

FIG. 6B shows the estimated fetal DNA fraction versus the actual fetal DNA fraction at 2 million reads. A linear regression fit to the data has an R squared of 0.9918 and a p-value less than 0.001.

Figure 6C:
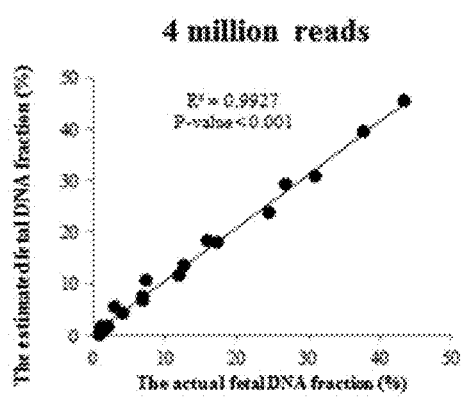

FIG. 6C shows the relationship at 4 million reads. A linear regression fit to the data has an R squared of 0.9927 and a p-value less than 0.001.

Figure 6D:
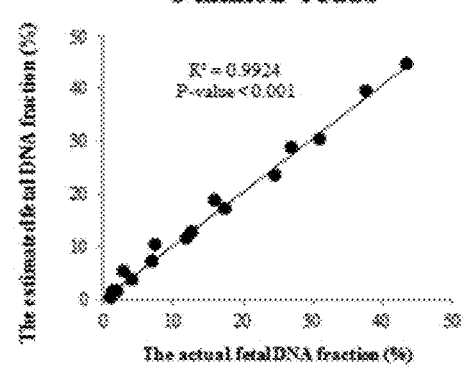

FIG. 6D shows the relationship at 8 million reads. A linear regression fit to the data has an R squared of 0.9924 and a p-value less than 0.001.

The R squared values are all above 0.99 regardless of the number of reads. The p-values remain less than 0.001 no matter the number of reads. The results showed that even the use of 1 million reads can allow us to perform a prediction as good as the results through using 2, 4, 6, or 8 million reads.

E. Applicability of Methods

The fraction of non-maternal alleles present in maternal plasma of a pregnant female can be used to estimate the fetal DNA fraction. A linear relationship between the fractional fetal DNA concentration and the fraction of non-maternal alleles with a high R squared was present in the maternal plasma, which demonstrated the genotyping and sequencing errors are relatively constant given that consistent platforms are applied to the same data set. The predictive ability of this method has been validated in independent data sets. Accuracy may be improved with updated calibration curves for different sequencing or genotype platforms. The improved R squared in the second data set may be attributed to the improved accuracy of genotyping and sequencing systems [Yu S C et al. (2014), *Proc Natl Acad Sci USA*, 111: 8583-8588; Lo Y M D et al. (2010), *Sci Transl Med*, 2: 61ra91]. However, the different relative error (E %) observed between the two data sets are likely due to more samples exhibiting relatively lower fetal DNA fractions in the second data set.

Notably, sequencing depth is not a critical factor affecting the accuracy of the fetal DNA fraction estimation as demonstrated in downsampling analysis. This method may be accurately generalized to samples with different sequencing depths. The underlying reason may be that the portion of loci showing the non-maternal alleles in maternal plasma will proportionally increase or decrease as the sequencing depth varies. Then, the fraction of non-maternal alleles in maternal plasma may be a constant value across different sequencing depths.

Therefore, this method may eliminate the high demand for sequencing depth and could be readily applied to the real clinical practices since the amount of sequencing reads with ~15 million can be routinely achieved in the non-invasive prenatal diagnosis [Kim S K et al. (2015), Prenatal diagnosis: n/a-n/a].

The accuracy of the fetal DNA prediction should be higher than two previous non-polymorphism-based approaches [Yu S C et al. (2014), Proc Natl Acad Sci USA, 111: 8583-8588; Kim S K et al. (2015), Prenatal diagnosis: n/a-n/a], because the previous values for R squared statistics were 0.83 and 0.93 respectively, [Yu S C et al. (2014), Proc Natl Acad Sci USA, 111: 8583-8588; Kim S K et al. (2015), Prenatal diagnosis: n/a-n/a] which are lower than the counterpart of this study (The value of R squared was 0.99 in the second data set). Furthermore, this algorithm was able to accurately determine the low fetal DNA fraction of 5% (FIG. 5). This ability to measure the low fetal DNA fraction is particularly important because a considerable portion (around 5%) of the maternal plasma samples have fractional fetal DNA concentration less than 5% [Chiu R W et al. (2011), BMJ 342: c7401; Palomaki G E et al. (2011), Genet Med, 13: 913-920]. The accurate estimation of fetal DNA fraction may then allow precise filtering out of samples with low fetal DNA fractions in a quality-control step [Palomaki G E et al. (2011), Genet Med, 13: 913-920]. In addition, the degree of change in the amount of maternal plasma DNA from a chromosome involved in fetal aneuploidy show correlations with the fetal DNA fraction. Samples with data falling outside of the correlation curve are considered more likely to be false positives. Embodiments of estimating the fetal DNA fraction may help identify false results. On the other hand, certain pregnancy-related conditions, such as preeclampsia and trisomy 18, are associated with perturbed fetal DNA fractions in maternal plasma. Thus, a better estimation of the fetal DNA fractions would allow more sensitive detection of those conditions associated with perturbed amounts of fractional fetal DNA concentrations.

As the massively parallel sequencing-based clinical diagnosis is increasingly recognized and progressively applied to clinical practices, personalized genotypes may be available for each individual. Thus, the maternal genotype-assisted fetal DNA fraction estimation could be readily integrated into currently existing approaches used in non-invasive prenatal diagnosis. Embodiments using the sequence reads of alleles provide a generic approach for the accurate estimation of the fractional fetal DNA concentration. Because there is a paucity of methods developed to accurately estimate the fractional fetal DNA concentration in the random sequencing based non-invasive prenatal diagnosis, this method would provide a useful tool to enhance one of the most rapidly adopted clinical utilities of noninvasive prenatal detection of fetal chromosomal aneuploidies [Agarwal A et al. (2013), Prenat Diagn, 33: 521-531], by allowing more accurate statistical interpretations of the sequencing result of the maternal plasma DNA.

F. Exemplary Method of Measuring Fetal DNA Fraction Using Amounts of Reads

Figure 7:
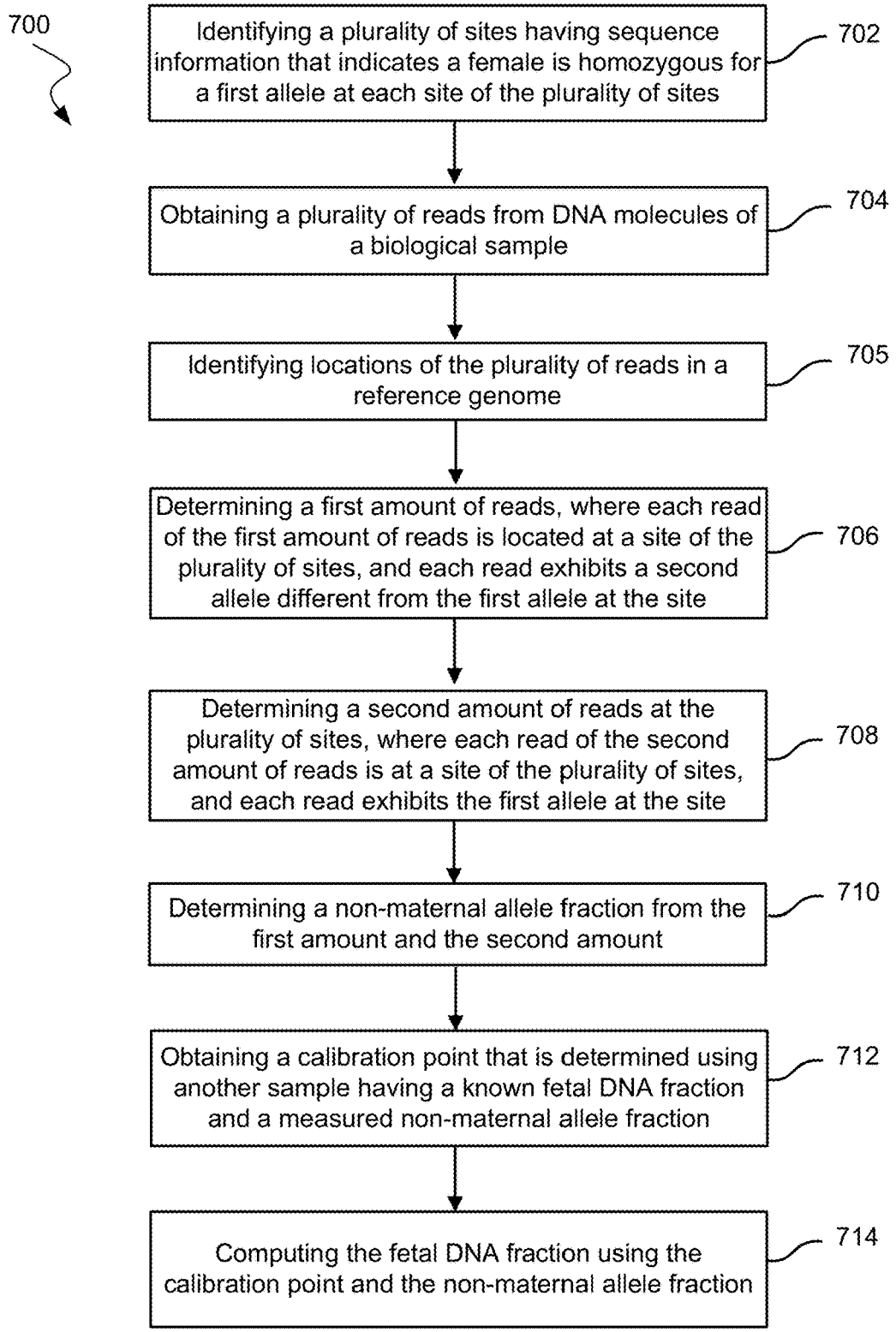
FIG. 7 shows a method of measuring fetal DNA fraction in a biological sample of a female pregnant with a fetus using amounts of reads according to embodiments of the present invention.

FIG. 7 shows an example method 700 of measuring a fetal DNA fraction in a biological sample of a female pregnant with a fetus. The biological sample includes maternal DNA molecules and fetal DNA molecules. Method 700 can be performed using a computer system.

At block 702, method 700 includes identifying a plurality of sites having sequence information that indicates the female is homozygous for a first allele at each site of the plurality of sites. As examples, the sequence information may be determined from a same sample (e.g., a different set of reads or a different aliquot of the sample), which may be plasma or other mixture of fetal and maternal DNA, or from a different sample of the female (e.g., from a sample of the buffy coat, a buccal swab, or a different sample of plasma). Regardless of the origin of the sample, the sequence information can comprise a separate data set of reads of DNA molecules, e.g., other reads from the same sample or a different sample. In some embodiments, the indication that the female is homozygous can be made based on only the first allele being detected at the particular site. In other embodiments, the indication can allow some reads having a different allele, but with the number of reads having the other allele at the site being below a threshold (e.g., a threshold for calling the site homozygous to within a specific statistical accuracy). Such an embodiment can be performed when a maternal-only sample (e.g., buffy coat) is used to obtain the sequence information. The sequence information may be obtained via any suitable technique, e.g., sequencing or proves, as is described herein.

The female may actually be homozygous at the plurality of sites. In some embodiments, however, the female may be sequenced at a shallow depth so that only a few alleles (e.g., one or two) are read at the sites, and the female may appear homozygous even though the female is heterozygous at the site. Identifying the plurality of sites may include obtaining a plurality of reads from DNA molecules of the biological sample. In other embodiments, identifying the plurality of sites at which the female appears homozygous may include identifying a plurality of sites from a plurality of reads of another biological sample (i.e., a second biological sample) that does not include fetal DNA samples. For example, this second biological sample may be a maternal buffy coat or buccal swab. Identifying the plurality of sites at which the female appears homozygous may include genotyping cells in the second biological sample from the female. In some embodiments, the analysis of the maternal genotypes does not need to be highly accurate and can be obtained from a shallow depth sequencing of maternal buffy coat, for example, but not limited, less than 0.1×, 0.2×, 0.3×, 0.4×, 0.5×, 0.8×, 1×, 1.5×, 2×, 3×, 4×, 5×, and 10× coverage of a haploid human genome. In some embodiments, the plurality of reads may be limited to only reads occurring at a second plurality of sites that are in a reference database for sites known to have SNPs.

At block 704, method 700 includes obtaining a plurality of reads from DNA molecules of the biological sample. The plurality of reads may be obtained from a sequencing device or from a data storage device. Method 700 may also include receiving the biological sample before obtaining the reads. The reads may be limited to sites that are identified in a database as corresponding to a biallelic site, i.e., a site with an SNP. A plurality of DNA molecules in the biological sample may be sequenced to obtain the reads. In other embodiments, a plurality of DNA molecules in the biological sample may be analyzed using a microarray of probes to obtain the reads.

At block 705, method 700 includes identifying locations of the plurality of reads in a reference genome. For example, the cell-free DNA molecules can be sequenced to obtain sequence reads, and the sequence reads can be mapped (aligned) to the reference genome. If the organism was a human, then the reference genome would be a reference human genome, potentially from a particular subpopulation. As another example, the cell-free DNA molecules can be analyzed with different probes (e.g., following PCR or other amplification), where each probe corresponds to a genomic location At block 706, method 700 includes determining a first amount of reads. Each read of the first amount of reads is located at a site of the plurality of sites, and each read exhibits a second allele different from the first allele of the female at the site. In some cases, the first amount of reads is the amount of reads of non-maternal alleles. The second allele may be limited to an allele identified in a database as corresponding to a biallelic site. Not all sites of the plurality of sites may include a read that exhibits the second allele. In fact, a portion of the sites of the plurality of sites may not include a read exhibiting the first allele.

At block 708, a second amount of reads at the plurality of sites may be determined. Each read of the second amount of reads is located at a site of the plurality of sites, and each read exhibits the first allele at the site. In some embodiments, the second amount may include the reads of the identical alleles summed with the first amount of reads that exhibit an allele different from an allele of the female. In other words, the second amount may be either the sum of A+B as shown in FIG. 1, or the second amount may be the sum of A. Determining the second amount of reads may be determined implicitly from the total number of reads. The total number of reads may be the second amount of reads.

At block 710, a non-maternal allele fraction may be determined from the first amount and the second amount. The non-maternal allele fraction may include the first amount divided by the second amount. The non-maternal allele fraction may include a number converted to a percentage. In some embodiments, the non-maternal allele fraction may include the second amount divided by the first amount.

At block 712, a calibration point that is determined using another sample having a known fetal DNA fraction and a measured non-maternal allele fractions may be obtained. The calibration point may be one calibration point of a plurality of calibration points, and the plurality calibration points may constitute a calibration curve. The calibration curve may be computed by determining fetal DNA fractions for a plurality of other samples from a plurality of pregnant females. The fetal DNA fraction for each other sample of the plurality of other samples may include identifying a second plurality of sites where at each site, the fetus is heterozygous and the pregnant female is homozygous. In some embodiments, the fetal DNA fraction may be determined using the Y chromosome of male fetuses. The plurality of reads from DNA molecules of the other sample may be obtained. The plurality of reads may be equal to or similar to the number of the plurality of reads from DNA molecules of the first biological sample. A third amount of reads having a fetal-specific allele at the second plurality of sites may be determined. A fourth amount of reads having a shared allele at the second plurality of sites may be determined. The fetal DNA fraction may be determined using the third amount and the fourth amount. Non-maternal fractions may be computed for the plurality of samples. The fetal DNA fractions and the non-maternal fractions may be fit to a linear or other function. The linear or other function may describe the calibration curve.

At block 714, the fetal DNA fraction may be computed using the calibration point and the non-maternal allele fraction. The non-maternal allele fraction may be compared to a calibration point of the calibration curve. The computed fetal DNA fraction may equal the fetal DNA fraction corresponding to the same or similar non-maternal allele fraction on the calibration curve. If the calibration curve is represented by an equation, the fetal DNA fraction may be the calculated result of substituting the non-maternal allele fraction into the equation.

Figure 11:
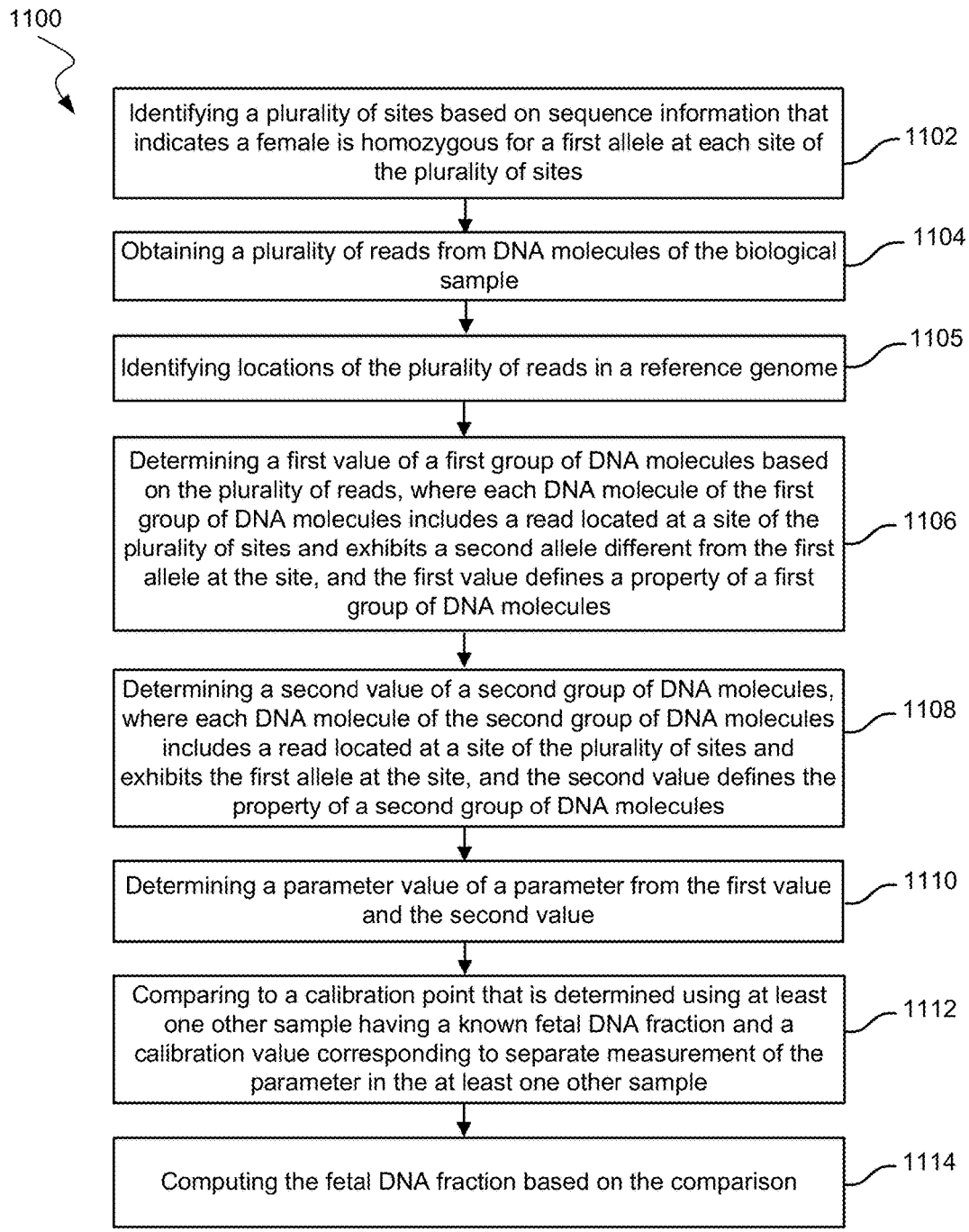
FIG. 11 shows a method of measuring fetal DNA fraction in a biological sample of a female pregnant with a fetus according to embodiments of the present invention.

G. Exemplary Method of Measuring Fetal DNA Fraction Using Properties of DNA Molecules FIG. 11 shows an example method 1100 of measuring a fetal DNA fraction in a biological sample of a female pregnant with a fetus. Method 1100 may use a value defining a property of a group of DNA molecules. The property may include a size parameter of the group of molecules or an amount of sequence reads of the group of molecules.

At block 1102, method 1100 includes identifying a plurality of sites having sequence information that indicates the female is homozygous for a first allele at each site of the plurality of sites. Identifying the plurality of sites may be by any operation described herein, including operations described in method 700.

At block 1104, method 1100 includes obtaining a plurality of reads from DNA molecules. Obtaining the plurality of reads may be by any operation described herein, including operations described in method 700.

At block 1105, method 1100 includes identifying locations of the plurality of reads in a reference genome. The reference genome may be the human genome. Identifying locations of the reads may include aligning the reads to the reference genome or using probes. Identifying locations may be by any operation described herein, including the operation described for block 705 in method 700.

At block 1106, method 1100 includes determining a first value of the first group of DNA molecules. Each DNA molecule of the first group of DNA molecules may include a read is located at a site of the plurality of sites. Each read may exhibit a second allele different from the first allele at the site. The first value may define a property of the first group of DNA molecules. For example, the first value may be the number of reads located at the plurality of sites and having the second allele, as in method 700. Determining the first value may further include measuring sizes of the first group of DNA molecules, where the first size value is of a first size distribution of the first group of DNA molecules. In embodiments, the first value may be a size parameter. The size parameter may be a number of molecules with a size in a certain range or the cumulative frequency of molecules under a certain size, e.g., a first cumulative frequency for DNA molecules having a maximum size in the first group of DNA molecules.

At block 1108, method 1100 includes determining a second value of a second group of DNA molecules. Each DNA molecule of the second group of DNA molecules may include a read located at a site of the plurality of sites. Each read may exhibit the first allele at the site. The second group of DNA molecules may also be from the same biological sample as the first group of DNA molecules or may be from another biological sample (e.g., a maternal DNA-only sample such as a buffy coat or buccal swab). Determining the second value may further include measuring sizes of the second group of DNA molecules, where the second size value is of a first size distribution of the second group of DNA molecules. The second value may define the property of the second group of DNA molecules. For example, if the first value is a size parameter, the second value may also be a size parameter. The second value may be the second number of reads located at the plurality of sites and having the first allele.

At block 1110, a parameter value of a parameter may be determined from the first value and the second value. The parameter may include a ratio of the first value divided by the second value.

At block 1112, method 1100 may include comparing the parameter value to a calibration point that is determined using at least one other sample (e.g., a calibration sample) having a known fetal DNA fraction and a calibration value corresponding to separate measurement of the parameter in the at least one other sample. The calibration point may be one calibration point of a plurality of calibration points, and the plurality calibration points may constitute a calibration curve. The calibration curve may be computed by determining fetal DNA fractions for a plurality of other samples from a plurality of pregnant females, similar to the operation in block 712 of method 700. The parameter values may be computed for the plurality of other samples. The fetal DNA fractions and the parameters may be fit to a linear or other function. The linear or other function may describe the calibration curve.

At block 1114, the fetal DNA fraction may be computed based on the comparison. The computed fetal DNA fraction may equal the fetal DNA fraction corresponding to the same or similar parameter value on the calibration curve. If the calibration curve is represented by an equation, the fetal DNA fraction may be the calculated result of substituting the parameter value into the equation.

H. Measuring Fetal DNA Fraction Using Size Parameters

The size of DNA molecules with non-maternal alleles and/or the size of DNA molecules with maternal alleles may be used to estimate the fetal DNA fraction. Fetal DNA has been found to be shorter than maternal DNA in maternal plasma (Lo Y M D et al. Sci Transl Med. 2010; 2:61ra91). As a result, DNA molecules with non-maternal alleles should be shorter on average than DNA molecules with maternal alleles in maternal plasma.

As an example, a maternal plasma with a 20% fetal DNA fraction is genotyped by a microarray approach (Illumina). Sites where the maternal DNA was homozygous and a non-maternal allele was present in the plasma were identified. The sizes of the DNA molecules with these sites were compared for maternal alleles and non-maternal alleles.

Figure 12A:
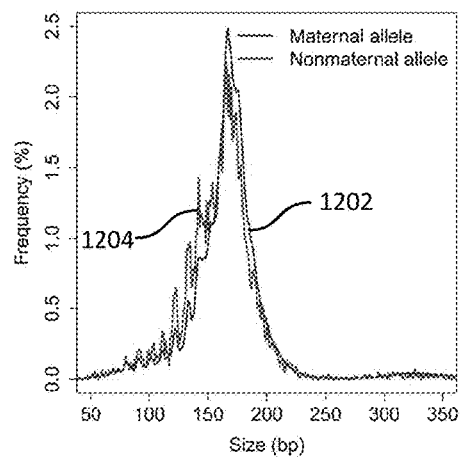
FIGS. 12A, 12B, 12C, and 12D illustrate the relationship between DNA molecule sizes for maternal and non-maternal alleles according to embodiments of the present invention.

FIG. 12A shows the size distribution of DNA molecules with maternal alleles and non-maternal alleles. The x-axis is the size of a DNA molecule in base pairs. The y-axis is the frequency of a given size as a percentage. Line 1202 is the size distribution of the DNA molecules with the maternal alleles, and line 1204 is the size distribution of the DNA molecules with the non-maternal alleles. Line 1204 is generally to the left of line 1202, suggesting that DNA molecules with non-maternal alleles are generally shorter than DNA molecules with maternal alleles.

Figure 12B:
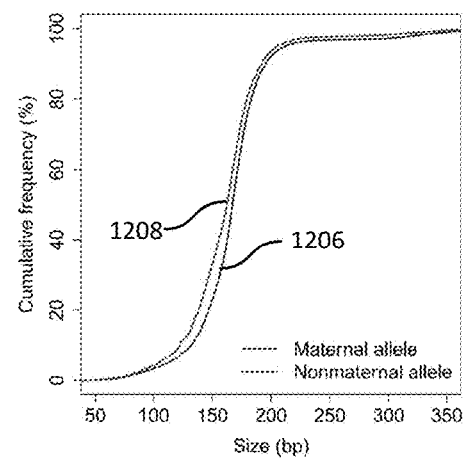

FIG. 12B shows the cumulative frequency of the sizes of the DNA molecules from FIG. 12A. The x-axis is the size of a DNA molecule in base pairs. The y-axis is the cumulative frequency as a percent. Line 1206 is the cumulative frequency curve for sizes of DNA molecules with maternal alleles. Line 1208 is the cumulative frequency curve for sizes of DNA molecules with non-maternal alleles. Line 1208 is above line 1206, indicating that DNA molecules with non-maternal alleles are shorter than DNA molecules with maternal alleles.

Figure 12C:
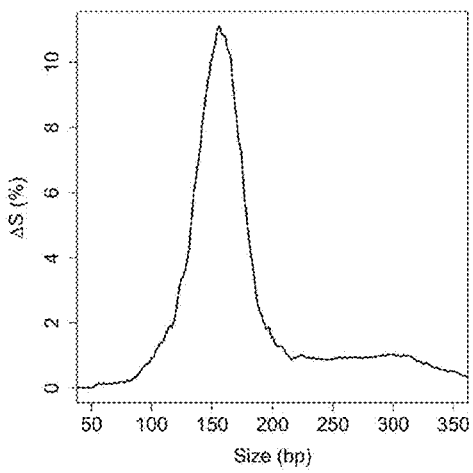

FIG. 12C shows $\Delta S$, the difference between the two cumulative frequency curves (line 1206 and line 1208). The x-axis is the size of a DNA molecule in base pairs. The y-axis is $\Delta S$, the difference between the two cumulative frequency curves. The maximum value of $\Delta S$ is about 150 bp. As a result, for DNA molecules of sizes less than or equal to 150 bp, the DNA molecules would be relatively enriched for non-maternal alleles. The $\Delta S$ at 150 bp, denoted as $\Delta S_{150}$, was quantified for 32 samples with 8 million paired-end sequence reads to test its suitability in estimating fetal DNA fraction.

Figure 12D:
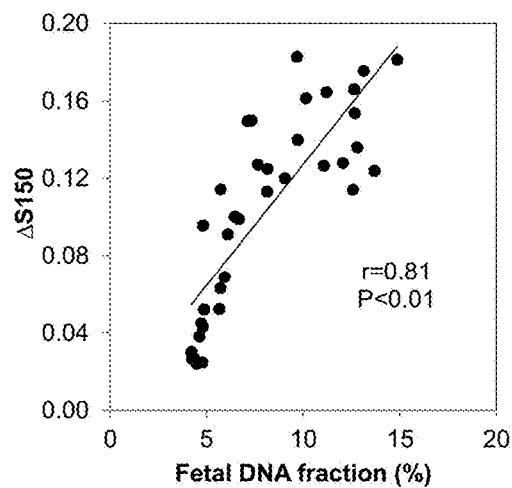

FIG. 12D shows the relationship between $\Delta S_{150}$ and fetal DNA fraction for the 32 samples. The x-axis is the fetal DNA fraction as a percent. The y-axis is $\Delta S_{150}$, the difference between the cumulative frequency curve of DNA molecules with non-maternal alleles and the cumulative frequency curve of DNA molecules with maternal alleles at a length of 150 bp. $\Delta S_{150}$ is positively correlated with the fetal DNA fraction. In other words, a higher amount of short DNA molecules carrying the non-maternal alleles suggest a higher fetal DNA fraction. A linear regression is fit to the data. The linear fit has an R squared of 0.81 (p<0.01). The DNA molecules with the maternal alleles include DNA molecules that are fetal DNA, but still carry the maternal allele. Thus, the $\Delta S_{150}$ is not expected to reflect the actual size difference between maternal DNA and fetal DNA.

In some embodiments, the $\Delta S$ may be at sizes other than at 150 bp. For example, the $\Delta S$ may be at 50, 60, 70, 80, 90, 100, 110, 120, 130, 140, 160, 170, 190, 200, or 210 bp. Other size parameters may also be used. The size difference can be between any statistical value of size distributions for the two groups. For example, a difference in a median size of the first group of DNA molecules and the second group of DNA molecules can be used. As another example, a maximum in a cumulative frequency by size between the first group and the second group. Any size value described in U.S. Patent publications 2011/0276277 and 2013/0237431 can be used.

A calibration curve between the size parameter and the fetal DNA fraction can be used. The calibration curve may relate the fetal DNA fraction to the size parameter for other samples. The fetal DNA fraction for the other samples may be determined by any method described herein. The size parameter may then be measured for the other samples and plotted against the fetal DNA fraction. A linear regression or other regression would be fit to the data to determine a calibration curve. The size parameter of a biological sample of unknown fetal DNA fraction can then be compared to the calibration curve to estimate a fetal DNA fraction.

In these embodiments, size parameter based on the sizes of non-maternal allele DNA and maternal allele DNA may be used in estimating the fetal DNA fraction, even if the parameter does not reflect the sizes of fetal DNA and maternal DNA.

I. Exemplary Method of Measuring Fetal DNA Fraction Using Size Parameters

Figure 13:
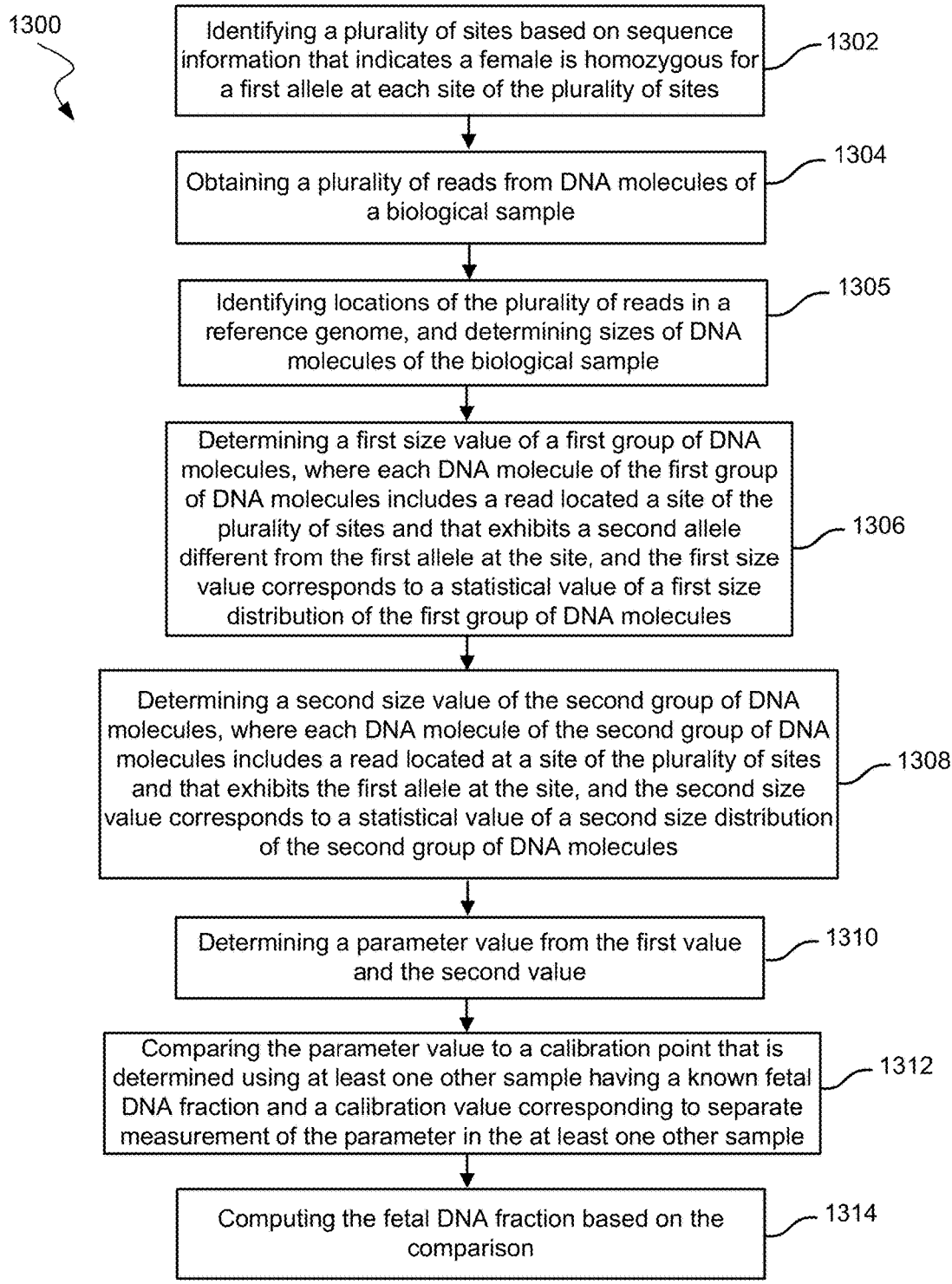
FIG. 13 shows a method of measuring fetal DNA fraction in a biological sample of a female pregnant with a fetus using size values according to embodiments of the present invention.

FIG. 13 shows an example method 1300 of measuring a fetal DNA fraction in a biological sample of a female pregnant with a fetus. Method 1300 may use a value defining a size of a group of DNA molecules. The value may be a value of a size parameter.

At block 1302, method 1300 includes identifying a plurality of sites based on sequence information that indicates the female is homozygous for a first allele at each site of the plurality of sites. Identifying the plurality of sites may be by any operation described herein, including as in method 700.

At block 1304, method 1300 includes obtaining a plurality of reads from DNA molecules of the biological sample. Obtaining the plurality of reads may be by any operation described herein, including as in method 700.

At block 1305, method 1300 includes identifying locations of the plurality of reads in a reference genome and determining sizes of DNA molecules of the biological sample. Identifying locations may be by any operation described herein, including the operation described for block 705 in method 700. Measuring sizes may be by electrophoresis or performed in silico.

At block 1306, method 1300 includes determining a first size value of a first group of DNA molecules. Each DNA molecule of the first group of DNA molecules may include a read located at a site of the plurality of sites. Each read may exhibits a second allele different from the first allele at the site. The first size value may correspond to a statistical value of a first size distribution of the first group of DNA molecules. The first size value may be a size parameter. The size parameter may be a number of molecules with a size in a certain range or the cumulative frequency of molecules under a certain size. As further examples, the size value may be a median size, a mode of a size distribution, or a mean size of the first group of DNA molecules.

At block 1308, method 1300 includes determining a second value of a second group of DNA molecules. Each DNA molecule of the second group of DNA molecules may include a read located a site of the plurality of sites. Each read may exhibit the first allele at the site. The second group of DNA molecules may also be from the biological sample or may be from another biological sample (e.g., a maternal DNA-only sample such as a buffy coat or buccal swab). As further examples, the size value may be a median size, a mode of size distribution, or a mean size of the second group of DNA molecules. The second size value may correspond to a statistical value of a second size distribution of the second group of DNA molecules. For example, if the first value is a size parameter, the second value may also be a size parameter.

At block 1310, a parameter value from the first value and the second value may be determined. The parameter may include a ratio of the first value divided by the second value.

At block 1312, method 1300 may include comparing the parameter value to a calibration point that is determined using at least one other sample (e.g., a calibration sample) having a known fetal DNA fraction and a calibration value corresponding to separate measurement of the parameter in the at least one other sample. The calibration point may be one calibration point of a plurality of calibration points, and the plurality calibration points may constitute a calibration curve. The calibration curve may be computed by determining fetal DNA fractions for a plurality of other samples from a plurality of pregnant females, similar to as described in method 700. The parameter values may be computed for the plurality of other samples. The fetal DNA fractions and the parameters may be fit to a linear or other function. The linear or other function may describe the calibration curve.

At block 1314, the fetal DNA fraction may be computed based on the comparison. The parameter value may be compared to a calibration point of the calibration curve. The computed fetal DNA fraction may equal the fetal DNA fraction corresponding to the same or similar parameter value on the calibration curve. If the calibration curve is represented by an equation, the fetal DNA fraction may be the calculated result of substituting the parameter value into the equation.

II. Analyzing DNA using Amount of Loci

To determine a maternal genotype or a fetal genotype, some embodiments do not require analysis of reads from a sample of only maternal DNA, only fetal DNA, or any DNA from only one subject. Indeed, some embodiments need not include highly accurate information about the maternal genotype. For example, determining what loci on the maternal genotype are homozygous need not be known with high statistical confidence or even any statistical confidence. Instead, methods can assume that certain loci are homozygous by the presence of only one or a few alleles in a sample containing both maternal DNA and fetal DNA. These methods often have shallow sequencing depths not considered adequate for confidently assessing alleles present at a locus. For example, determining that a locus is homozygous may be based on only one or two reads at the locus. As a result, sites identified as homozygous may only appear to be homozygous because the site has not been sequenced in enough depth.

Additionally, embodiments to analyze DNA can include analyzing the apparently homozygous loci for an alternative allele (e.g., non-maternal allele) in a sample containing both maternal DNA and fetal DNA. Analyzing the sample for the alternative allele may also be done at shallow sequencing depths. The shallow sequencing depths may result in few reads, sometimes only one or two reads, at a locus. The low number of reads at a locus may result in not sequencing any alternative allele that is actually present at a locus or undercounting the proportion of alternative alleles present at a locus. Because of these possible errors, techniques using a shallow sequencing depth would not be expected to accurately measure the fetal DNA fraction or other characteristics of a biological sample.

Moreover, identifying an alternative allele at a locus as a means to determine fetal DNA fraction would not be expected to work for any single locus. For any single locus, the alternative allele would either be present or not present. This binary outcome would not provide enough information for measuring the fetal DNA fraction or other characteristics of a biological sample.

However, methods described herein surprisingly can accurately measure the fetal DNA fraction or other characteristics of a biological sample when shallow sequencing is performed. These methods can provide useful information regarding the biological sample by using several loci, averaging results to minimize sequencing and other errors, and using calibration data. These methods improve over conventional methods, which may work well for only male fetuses, may need genotype information of either or both parents, or may need high sequencing depths.

A. General Approach

FIG. 8 shows an illustration of a method 800 of measuring fetal DNA fraction without obtaining a maternal genotype, a paternal genotype, or a biological sample containing only maternal DNA molecules.

Block 802 starts with a biological sample or biological samples. The biological sample(s) may be plasma, serum, blood, saliva, sweat, urine, tears, or other fluids from a female pregnant with a fetus. The biological sample may have a minimum fetal DNA molecule fraction of 1%, 2%, 3%, 4%, or 5%. The biological sample contains both maternal and fetal DNA molecules. The biological sample may be obtained by a needle administered by a medical professional. The biological sample may also be obtained noninvasively as part of a routine medical appointment.

Block 804 shows that sequencing reads are obtained from DNA molecules from the biological sample. The sequencing reads for any data set may be shallow or low-depth. For example the number of sequencing reads may be less than 0.1×, 0.2×, 0.3×, 0.4×, 0.5×, 0.8×, 1×, 1.5×, 2×, 3×, 4×, 5×, and 10× coverage of a haploid human genome. The sequencing of the DNA molecules may be performed by any suitable sequencing technique or system. The sequencing or the reads may be limited to sites with known and common SNPs, including SNPs in a reference database (e.g., dbSNP or HapMap).

Blocks 806 and 808 show two data sets of sequenced reads obtained from one or more biological samples. The two data sets may be data from two biological plasma DNA replicates (i.e., two different blood draws from the same patient at about the same time); one plasma sample split into two aliquots; one plasma sample and one constitutional genomic DNA sample (e.g., maternal buffy coat DNA, buccal swab DNA); or one plasma/serum sequencing data set randomly split into two sequencing data sets in silico. Accordingly, two samples may be obtained in block 802, with sequence reads obtained separately for each sample.

Block 810 depicts identifying an exclusive allele in each locus of a first set of loci. For illustrative purposes, reads 812 show a first set of loci 814 that is characterized by an exclusive, single allele at each locus of loci a-h. An allele is symbolized by a white or black square in FIG. 8. In reads 812, first set of loci 814 includes loci a-h. Loci a-h may not be consecutive loci. These loci are apparently homozygous because no locus shows the presence of two different alleles. Given only one or two reads at any locus in reads 812, characterizing any locus as homozygous cannot be done with a high statistical confidence. Indeed, for a locus with a single read, the locus would not normally be considered characterized as homozygous with any confidence. These loci may be limited to loci with known and common SNPs.

Block 816 shows identifying a second set of loci that exhibits an alternative allele. The second set of loci is identified from within first set of loci 814. Reads 818 show the alleles sequenced from the second data set. Loci a, c, f, and g show reads with an allele different from the allele(s) in reads 814 for the same loci. These loci show an alternative allele, because the allele is alternative from the allele in the first data set. Loci b, d, e, and h show reads with alleles that are the same allele as in reads 814. The second set of loci is therefore identified as loci a, c, f, and g.

Block 820 determines a first amount of loci. The first amount of loci may be determined from the first set of loci. In other embodiments, because the first set of loci is analyzed in the second data set, the first amount of loci may be determined from the second data set. The first amount may be a number of loci or a number of reads with the alleles. If the first amount is a number of loci, for reads 812, the number of loci illustrated is 8. The first amount may be limited to reads from DNA molecules with a certain size or a certain property. For example, the first amount may be the number of loci for DNA molecules having a certain absolute size or a certain size relative to other DNA molecules. The number of reads with the alleles may be a count of the alleles read. In reads 812, the number of reads with the alleles is 11. In certain embodiments, the average number of reads with the alleles may equal to number of loci if the each loci averages about one allele read.

Block 822 determines a second amount of loci in the second set of loci. The second amount may be a number of loci or a number of reads with the alleles. The second amount should be commensurate with the first amount and have the same units, but the first amount and the second amount in some embodiments may have different units. If the second amount is the number of loci, then the second amount determined from the second set of reads 818 is 4. If the second amount is the number of reads with the alleles, the second amount in reads 818 is 6. Because the first set of loci in the second data set is analyzed for the second set of loci, the first amount of loci may, in some instances, be considered to be determined from the second data set in addition to the first data set.

Block 824 determines an apparent allelic discrepancy (AAD) from the first amount and the second amount. AAD is a parameter to quantify the proportion of sites showing the alternative allele in the second data set and not present in the first data set. AAD may be calculated by the second amount divided by the first amount, as shown in block 824. In other embodiments, AAD may be calculated from the second amount divided by the amount of maternal alleles only (i.e., the difference between the second amount and the first amount). Calculating AAD may include a multiplicative factor and/or the reciprocals of the described calculations. AAD may be considered a normalized parameter of the second amount.

Block 826 shows analyzing the biological sample using the AAD. Analyzing the biological sample may include computing a fetal DNA fraction from AAD using a calibration curve. The calibration curve describes the relationship between fetal DNA fraction and AAD, as shown in graph 828. The calibration curve may be determined based on actual fetal DNA fractions and AAD values from other biological samples. The number of sequenced reads for the data points in the calibration curve may be similar to the number of sequencing reads in the biological sample with the unknown fetal DNA fraction. In other words, the AAD data from samples with known fetal DNA fractions should be at similar or the same sequencing depth as for the biological with the unknown fetal DNA fraction. For example, the calibration curve may be at a sequencing depth of within 1×, 5×, 10×, 15×, or 20× of the sequencing depth of the DNA molecules from the biological sample. In some embodiments, the calibration curve may be limited to samples with similar genetic backgrounds as the mother, father, or fetus. For example, the calibration curve may be narrowed to AAD data from samples from people of the same or similar ethnic group. Calibration curves may also be limited to specific haplotypes or haplotype blocks. Accordingly, several calibration curves could be used for the same sample, for several genomic regions, including haplotypes. In some embodiments, AAD may be used to non-invasively test for twin zygosity.

As the sequencing depth increases, the proportion of loci identified as having a non-maternal allele would increase as more and more non-maternal alleles at loci are sequenced. As a result, at high sequencing depths, the proportion of loci with a non-maternal allele and the AAD value would not be expected to vary with fetal DNA fraction. The sequencing depth may be limited to a maximum of 5×, 10×, 15×, 20×, or 25× coverage to avoid a region where the AAD value does not depend on the fetal DNA fraction. A biological sample may still be sequenced at high sequencing depths above this maximum, but the resulting data may then be downsampled randomly to generate a sequencing read data set with a sequencing depth below the maximum.

B. Exemplary Method of Measuring Fetal DNA Fraction

Figure 9:
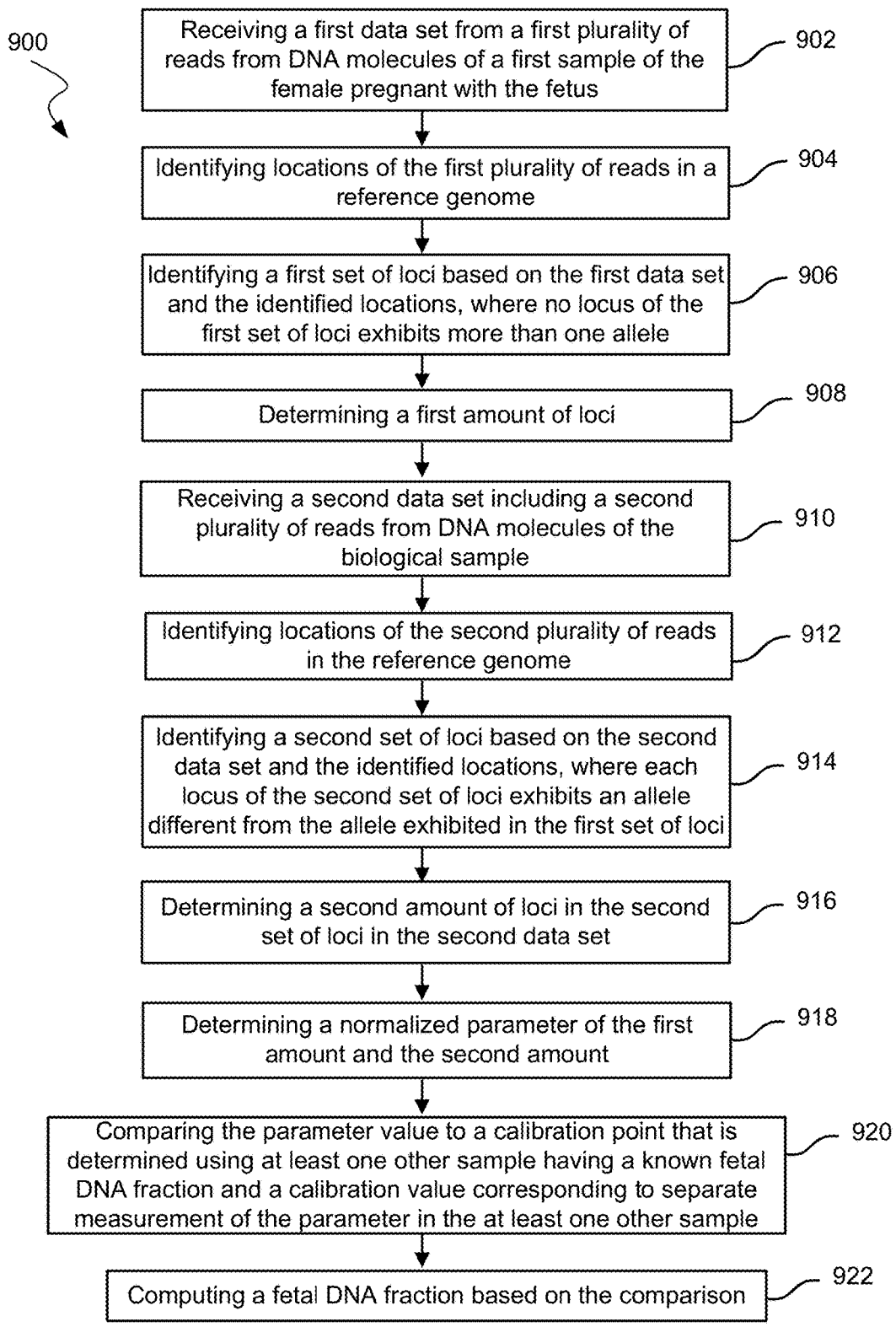
FIG. 9 shows a method of measuring a fetal DNA fraction in a biological sample of a female pregnant with a fetus using amounts of loci according to embodiments of the present invention.

FIG. 9 shows a method 900 of measuring a fetal DNA fraction in a biological sample of a female pregnant with a fetus. The biological sample includes maternal DNA molecules and fetal DNA molecules. The biological sample may be any biological sample described herein.

In block 902, method 900 includes receiving a data set from a plurality of reads from DNA molecules of a first sample of the female pregnant with the fetus. The data set may be received by a computer system from a sequencing device or a data storage device. The first sample may or may not be the biological sample. The first sample may have only maternal DNA and no fetal DNA, such as a buffy coat or a buccal swab.

In block 904, method 900 includes identifying locations of the first plurality of reads in a reference genome. Identifying the locations may be by any operation described herein, including the operation described for identifying sites in block 704 in method 700.

In block 906, method 900 includes identifying a first set of loci based on the first data set and the identified locations. No locus of the first set of loci exhibits more than one allele. In other words, each locus of the first set of loci is monoallelic and appears homozygous. The first set of loci may be chosen from a set of loci from a reference database. In other words, the first set of loci may be a subset of the set of loci from the reference database, with each loci of the first set of loci in the set of loci from the reference database. The set of loci may be known to include single nucleotide polymorphisms (SNPs) or a high instance of heterozygosity. The reference database may include The Short Genetic Variations database (dbSNP) or HapMap databases. The set of loci may be narrowed to certain loci known to have a high probability of heterozygosity in certain ethnic or other genetic groups similar to the ethnic or genetic group of the mother or the fetus.

The plurality of reads may be at shallow depth. For example, the depth of reads may be less than or equal to 10×, less than or equal to 5×, less than or equal to 4×, less than or equal to 3×, less than or equal to 2×, less than or equal to 1×, or less than or equal to 0.5× in embodiments. For a haploid human genome, 1× coverage is approximately 50 million reads for a size of 50 bp. The number of reads may be less than or equal to 50 million reads, including less than or equal to 30 million reads, 20 million reads, 15 million reads, less than or equal to 10 million reads, less than or equal to 8 million reads, less than or equal to 5 million reads, less than or equal to 4 million reads, less than or equal to 2 million reads, or less than or equal to 1 million reads. A locus may have a total of one or two reads. A plurality of loci in the first set of loci, including over 10%, over 20%, over 30%, over 40%, over 50%, over 60%, over 70%, over 80%, or over 90% of all loci in the first set of loci may have a maximum of one or two reads. The maximum number of reads in any locus of the first set of loci may be 1, 2, 3, 4, 5, 6, 7, 8, 9, or 10.

In block 908, method 900 includes determining the first amount of loci. The first amount may be the number of loci in the first set of loci from the first data set or may be the total number of alleles read in the first set of loci. In other embodiments, the first amount may be determined from the number of loci in the first set of loci from the second data set.

In block 910, a second data set from the plurality of reads from DNA molecules of the biological sample may be received. The second data set may be received by a computer system from a sequencing device or a data storage device.

In block 912, method 900 includes identifying locations of the second plurality of reads in a reference genome. Identifying the locations may be by any operation described herein, including the operation described for identifying sites in block 704 in method 700.

In block 914, a second set of loci is identified based on the second data set and the identified locations. Each locus of the second set of loci exhibits an allele different from an allele exhibited in the first set of loci. In other words, each locus of the second set of loci may show a non-maternal allele, while each corresponding locus in the first set of loci may show only maternal alleles. Each read in the second data set may be different from each read in the first data set. In some embodiments, the first data set may be half of the plurality of reads, and the second data set may be the other half of the plurality of reads.

In block 916, method 900 includes determining a second amount of loci in the set of loci in the second data set. The second amount may be the number of loci in the second set of loci or may be the total number of alleles read in the second set of loci. The second amount may be limited to reads from DNA molecules having a certain size. For example, the reads used for the second amount may be restricted to reads from a first plurality of DNA molecules having a minimum average size difference from a second plurality of DNA molecules. The second plurality of DNA molecules may include the DNA molecules with sequence reads used for the first set of loci. The second plurality of DNA molecules may include all DNA molecules sequenced in the biological sample. The minimum size difference may be 5 bp, 10 bp, 20 bp, 30 bp, or 40 by in embodiments. The sizes of the first plurality or second plurality of DNA molecules may be measured, or the sizes of the first plurality or second plurality of DNA molecules may be received.

In block 918, a normalized parameter of the first amount and the second amount may be determined. In some embodiments, the normalized parameter may include the second amount divided by the first amount. The normalized parameter may then be a ratio of the number of apparently non-maternal alleles to the number of maternal alleles. In other embodiments, the normalized parameter may include the second amount divided by the sum of the first amount and the second amount. In these embodiments, the normalized parameter may be the ratio of the number of apparently non-maternal alleles to the total number of alleles. The normalized parameter may also be the reciprocal of any of these calculations. AAD is an example of a normalized parameter.

In block 920, method 900 includes comparing the parameter value to a calibration point that is determined using at least one other sample (e.g., a calibration sample) having a known fetal DNA fraction and a calibration value corresponding to separate measurement of the parameter in the at least one other sample. The calibration point may be one calibration point of a plurality of calibration points. The plurality of calibration points may constitute a calibration curve. The calibration curve may be a curve fitted to data points of known fetal DNA fraction and normalized parameters determined for different biological samples. Graph 828 is one example of a calibration curve. The calibration curve may be a linear regression of the data points. The calibration curve may have a slope that does not equal 1 and may be less than 1.

The calibration curve may be determined using a known fetal DNA fraction and a normalized parameter (i.e., a second normalized parameter) from another biological sample determined by a similar method as the normalized parameter (i.e., the first normalized parameter) from the biological sample currently being analyzed. The second normalized parameter may also be determined from operations similar to blocks 902 to 918. The number of reads associated with the loci in the data sets from the other biological sample may be about equal to the number of reads in the current biological sample. The number of reads may be within 1×, 5×, or 10× of each other.

In block 922, a fetal DNA fraction is computed based on the comparison. The fetal DNA fraction may be the fetal DNA fraction in the calibration curve corresponding to the same value of the normalized parameter. In some embodiments, the fetal DNA fraction may be interpolated between two fetal DNA fractions for two values of the normalized parameter. In other embodiments, the calibration curve may be a linear equation, of the form y=mx+b, where y is the fetal DNA fraction, x is the normalized parameter, and m and b are parameters fitted to the calibration curve.

C. Experimental Results for Fetal DNA Fraction

Using AAD to measure fetal DNA fraction was tested using 24 plasma samples from 24 pregnant women carrying male fetuses, with each sample having an average of 8.1 million sequence reads (range: 7.1~10.3 million). Of the 24 samples, 14 samples were used to establish a calibration curve modeling the relationship between the actual fetal DNA fractions and AAD values. The actual fetal DNA fractions were determined by the proportion of reads derived from Y chromosome (Hudecova I et al, PLoS One. 2014; 9:e88484). To calculate AAD values, each sample of the 14 samples was divided randomly into two data sets. In the first data set, a first set of loci showing one and only one type of allele was identified. In the second data set, each locus of the first set of loci was analyzed to determine if an alternative allele was present. Loci with an alternative allele constituted the second set of loci. AAD was calculated as the number of loci in the second set of loci divided by the number of loci in the first set of loci multiplied by 100%.

Figure 10A:
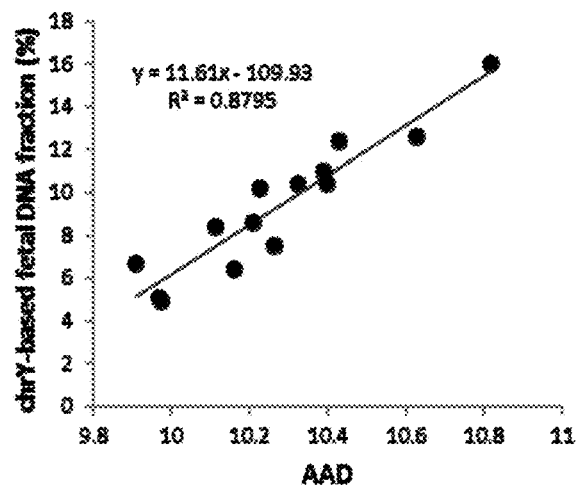
FIG. 10A shows a calibration curve from a linear regression model of the fetal DNA fractions and apparent allelic discrepancy (AAD) values according to embodiments of the present invention.

FIG. 10A shows the calibration curve from a linear regression model of the fetal DNA fractions and AAD values. The y-axis shows the fetal DNA fraction derived from the Y chromosome, and the x-axis shows the AAD value. The linear regression has a slope of 11.61 and an y-intercept of −109.93. The R squared value is 0.8795.

Figure 10B:
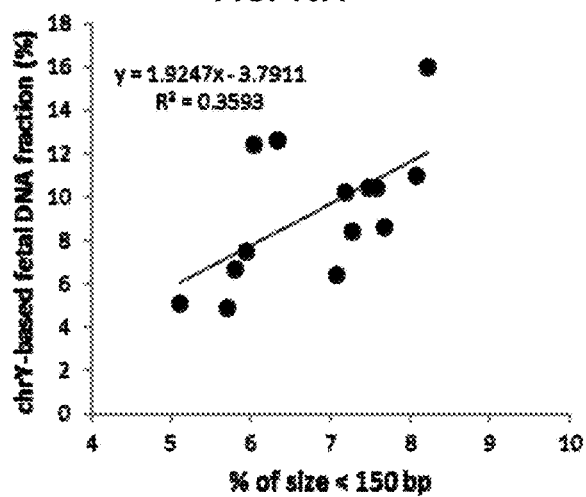
FIG. 10B shows a graph of a linear regression based on fetal DNA fractions and the proportions of short DNA molecules according to embodiments of the present invention.

FIG. 10B shows a linear regression based on the fetal DNA fractions and the proportions of short DNA molecules. The y-axis shows the fetal DNA fraction derived from the Y chromosome, and the x-axis shows the percentage of DNA molecules with a size less than 150 by in the sample. Fetal DNA fraction has been estimated based on the size of DNA molecules (Yu S C et al, Proc Natl Acad Sci USA. 2014; 111: 8583-8). The linear regression has a slope of 1.9247 and an y-intercept of −3.7911. The R squared value is 0.3593.

For this data set, determining the fetal DNA fraction from AAD values gave a higher correlation than determining the fetal DNA fraction from the proportion of shorter DNA molecules as indicated by the R squared values. With a higher R squared value, AAD-based fetal DNA fraction estimation would be more accurate than the size profile-based approach.

To test the generalizability of AAD-based calibration curve of FIG. 10A, the remaining 10 samples from 10 pregnant females were sequenced. Each sample of the 10 samples was divided randomly into two data sets. In the first data set, a first set of loci showing one and only one type of allele was identified. In the second data set, each locus of the first set of loci was analyzed to determine if an alternative allele was present. Loci with an alternative allele constituted the second set of loci. AAD was calculated as the number of loci in the second set of loci divided by the number of loci in the first set of loci multiplied by 100%.

The fetal DNA fractions for the AAD values from the 10 samples was determined from the calibration curve in FIG. 10A. In addition, the fetal DNA fractions were determined for the 10 samples by the proportion of reads derived from Y chromosome.

Figure 10C:
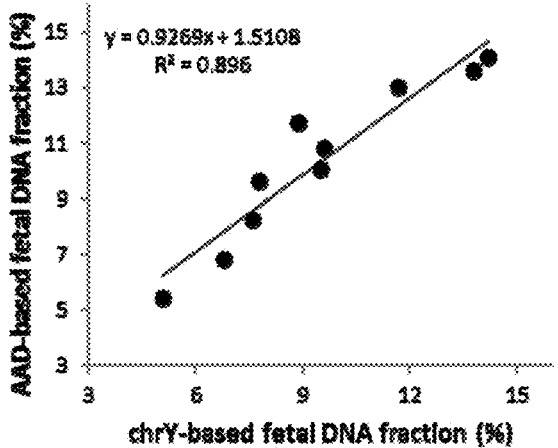
FIG. 10C shows a graph of fetal DNA fractions determined by AAD values against the fetal DNA fractions based on the proportion of reads derived from the Y chromosome according to embodiments of the present invention.

FIG. 10C shows the fetal DNA fractions determined by the AAD values on the y-axis against the fetal DNA fractions based on the proportion of reads derived from the Y chromosome. The fetal DNA fractions estimated by the AAD values were well correlated with the actual fetal DNA fractions, with an R squared of 0.896. The median deviation from the actual fetal DNA fraction was only 0.8%, suggesting a high accuracy of fetal DNA fraction prediction achieved. Thus, an AAD-based calibration curve is observed to be well-generalized into a new set of samples.

The accuracy of the AAD-based fetal DNA fraction estimation could be increased with a higher fetal DNA fraction in the sample, a reduced sequencing error rate, and using a calibration curve based on samples from individuals with similar genetic profiles.

D. Classifying Twin Zygosity with AAD

AAD can be used to classify whether twins are monozygotic or dizygotic. Dizygotic twins have fetuses with different genotypes. A locus with different genotypes means that at least one of the fetuses has a non-maternal allele. The proportion of loci with a non-maternal allele in a plasma sample with dizygotic fetuses would be higher than the proportion of loci in a plasma sample with a single fetus. For monozygotic twins, because the genotypes of the fetuses are identical, the proportion of loci in a plasma sample with monozygotic fetuses would not be expected to be higher than the proportion of loci in a plasma sample with a single fetus. The proportion of loci with non-maternal alleles would then be expected to be higher for dizygotic fetuses compared to monozygotic fetuses. As a result, the AAD calculated from the proportion of loci with non-maternal alleles would be expected to be higher, and the computed fetal DNA fraction would be expected to be higher for dizygotic fetuses.

FIG. 14 shows fetal DNA fractions calculated for six different sets of twins. Three sets of twins are monozygotic and three sets of twins are dizygotic. The fetal DNA fraction is estimated by two methods. In the first method, the fetal DNA fraction is estimated based on the size of DNA molecules (Yu S C et al, Proc Natl Acad Sci USA. 2014; 111: 8583-8). The size of the DNA molecules is not expected to vary based on the zygosity of the fetuses. In the second method, the fetal DNA fraction is estimated from an amount of loci (e.g., as described for embodiments using an AAD value). In the second method, the fetal DNA fraction is estimated from the AAD value. The AAD value is expected to vary based on the zygosity of the fetuses. FIG. 14 shows that the difference between the AAD-based fetal DNA fraction and the size-based fetal DNA fraction is greater for dizygotic twins compared to monozygotic twins. This difference in fetal DNA fraction estimates can be used to classify fetuses as either monozygotic or dizygotic.

To classify the zygosity of multiple fetuses, the fetal DNA fraction of a biological sample may be estimated using an AAD value, as described herein. This first fetal DNA fraction may then be compared with a cutoff value. The cutoff value may be determined to be some value greater than a second fetal DNA fraction of the biological sample. The second fetal DNA fraction may be estimated by a method where the estimated fetal DNA fraction does not vary based on the zygosity of the fetal DNA in the sample. For example, the estimated fetal DNA fraction may be based on the size profile of the DNA molecules in the biological sample. The cutoff value may be a certain absolute percentage greater than the second fetal DNA fraction. For example, in FIG. 14, a cutoff value may be between 2 and 4 absolute percent greater than the size-based fetal DNA fraction. The cutoff value may be an absolute percent greater, a relative percent greater, or a multiple of a standard deviation greater than the second fetal DNA fraction.

If the computed fetal DNA fraction is greater than the cutoff value, then the fetuses may be classified as dizygotic. If the computed fetal DNA fraction is less than the cutoff value, then the fetuses may be classified as monozygotic. In some embodiments, two cutoff values may be used, with a first cutoff value greater than a second cutoff value. If the computed fetal DNA fraction is greater than or equal to the first cutoff value, then the fetuses may be classified as dizygotic. If the computed fetal DNA fraction is less than or equal to the second cutoff, then the fetuses may be classified as monozygotic. If the computed fetal DNA fraction is between the two cutoff values, the fetuses may be classified as indeterminate for zygosity. The fetuses may then undergo further zygosity testing.

E. AAD with Loci Having a Certain Size

The calculation of AAD can be based on identifying a non-maternal allele through characteristics other than the sequence read. For example, as explained above, fetal DNA is shorter than maternal DNA. As a result, a long DNA molecule may likely include a maternal allele, while a short DNA molecule may likely include a non-maternal allele. Characteristics that indicate a non-maternal allele may be related to a size parameter of the DNA molecules in loci. The size parameter may be a certain absolute size or a certain size relative to other DNA molecules.

Identifying loci with non-maternal alleles may be based on a size difference from a maternal allele. A larger fetal DNA fraction may correlate with a larger proportion of sites with molecules in one data set showing at least a certain size difference from molecules in another data set.

As an example, shallow-depth sequence data from one aliquot with maternal DNA from a pregnant female was analyzed, and a first set of loci that have DNA molecules with lengths greater than 166 bp are identified. A second aliquot with maternal and fetal DNA from the same pregnant female was sequenced at shallow depth. In the data from the second aliquot, a second set of loci with DNA molecules having a size parameter (size value) shorter than 143 bp are identified. In other words, the difference between the size parameters of the DNA molecules of the two aliquots at a given locus is at least 23 bp. The number of loci in the second set of loci divided by the number of loci in the first set of loci yields the proportion of loci that have a size difference of at least 23 bp. The fetal DNA fraction for the pregnant female was also determined. This process was repeated for 23 additional pregnant females and the results were plotted. The calculation can also be done by first determining loci with a size value below a size threshold, and then determining a proportion of those loci having a size value above a second threshold in a different aliquot.

Figure 15:
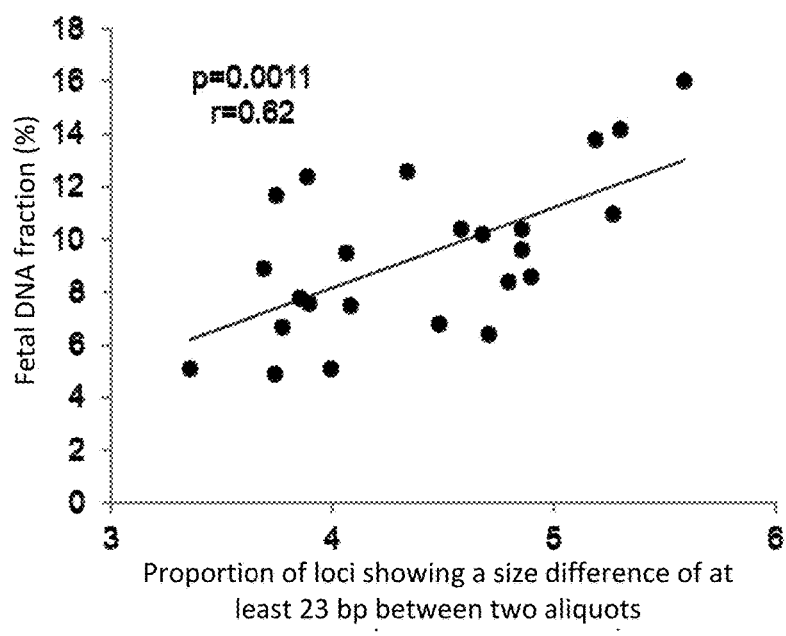
FIG. 15 is a graph of the relationship between fetal DNA fraction and loci showing a size difference according to embodiments of the present invention.

FIG. 15 shows the relationship between fetal DNA fraction and loci showing a size difference. The x-axis is the proportion as a percentage of loci showing a size difference of at least 23 bp between two aliquots. The y-axis is the fetal DNA fraction. A positive relationship is seen between fetal DNA fraction and the proportion of loci showing a size difference. The R squared is 0.62 (p=0.0011).

The correlation between proportion of loci showing a size difference and fetal DNA fraction shows that the proportion of loci showing a size difference may be used as a parameter (similar to AAD) to estimate fetal DNA fraction. The size difference does not have to be 23 bp. In other embodiments, the size difference may be at least 10, 20, 30, 40, or 50 bp. The data for each set of loci may not be from two different aliquots. The data may be obtained from the same biological sample.

A minimum size difference may be used as an additional factor for identifying non-maternal alleles. With shallow-depth sequencing, if an allele is found in a second data set that is different from a maternal allele in a first data set, the allele in the second data set may be a non-maternal allele. However, the allele in the second data set may alternatively be a maternal allele that was not sequenced in the first data set as a result of the shallow depths. If the allele in the second data set was a similar size as the maternal allele, then the allele is likely a second maternal allele. Thus, considering the size difference of the allele in the second data set may improve the identification of loci with non-maternal alleles.

Figure 16:
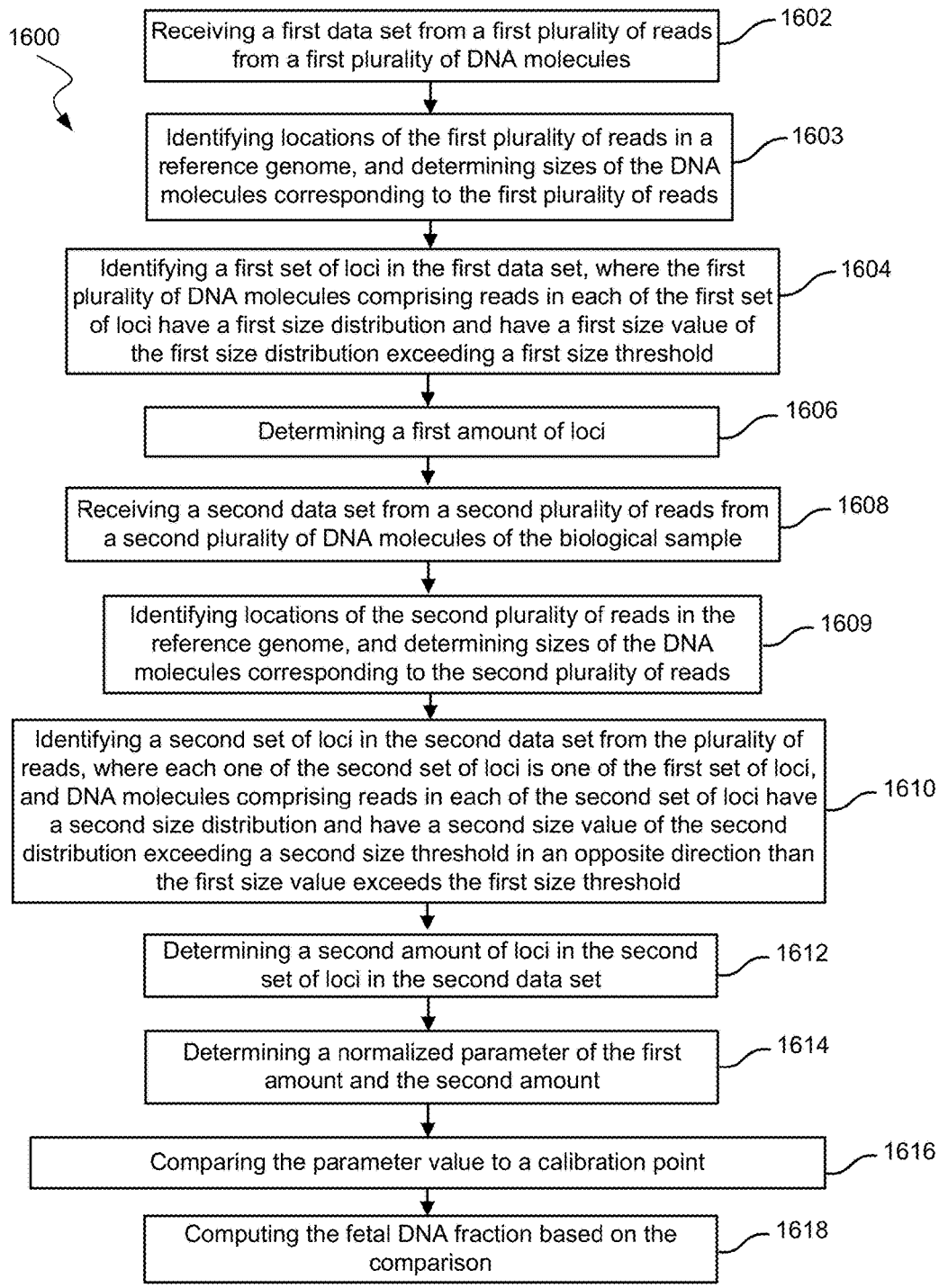
FIG. 16 shows a method of measuring fetal DNA fraction in a biological sample of a female pregnant with a fetus using amounts of loci having certain size DNA molecules according to embodiments of the present invention.

F. Exemplary Method of Measuring Fetal DNA Fraction with Loci Having DNA Molecules Showing a Size Difference FIG. 16 shows a method 1600 of measuring a fetal DNA fraction in a biological sample of a female pregnant with a fetus. The biological sample includes maternal DNA molecules and fetal DNA molecules. The biological sample may be any biological sample described herein.

In block 1602, method 1600 includes receiving a data set from a first plurality of reads from a first plurality of DNA molecules. The data set may be received by a computer system from a sequencing device or a data storage device. The first plurality of DNA molecules may or may not be in the biological sample. The first plurality of DNA molecules may come from a biological sample without fetal DNA.

In block 1603, method 1600 includes identifying locations of the first plurality of reads in a reference genome, and determining sizes of the DNA molecules corresponding to the first plurality of reads.

In block 1604, method 1600 includes identifying a first set of loci in the first data set. The first plurality of DNA molecules comprising reads in each of the first set of loci have a first size distribution and have a first size value of the first distribution exceeding a first size threshold. In some embodiments, all DNA molecules comprising reads in the first set of loci exceed the first size threshold. The first set of loci may be chosen from a set of loci from a reference database or considering other factors, as described in method 900. The plurality of reads may be at shallow depth.

In block 1606, method 1600 includes determining the first amount of loci. The first amount may be the number of loci in the first set of loci from the first data set.

In block 1608, a second data set from a second plurality of reads from a second plurality of DNA molecules of the biological sample may be received. The second data set may be received by a computer system from a sequencing device or a data storage device. Method 1600 may include measuring the sizes of the second plurality of DNA molecules, or receiving size information of the second plurality of DNA molecules.

In block 1609, method 1600 includes identifying locations of the second plurality of reads in a reference genome, and determining sizes of the DNA molecules corresponding to the second plurality of reads.

In block 1610, a second set of loci in a second data set from the plurality of reads is identified. Each locus of the second set of locus is a locus of the first set of locus. DNA molecules comprising reads in each of the second set of loci have a second size distribution and have a second size value of the second distribution exceeding a second size threshold in an opposite direction than the first size value exceeds the first size threshold.

The first size value may be larger than the first size threshold and the second size value may be smaller than the second size threshold, and the second size threshold may be smaller than the first size threshold. In other embodiments, the first size value may be smaller than the first size threshold, the second size value may be larger than the second size threshold, and the second size threshold is larger than the first size threshold In block 1612, method 1600 includes determining a second amount of loci in the set of loci in the second data set. The second amount may be the number of loci in the second set of loci.

In block 1614, a normalized parameter of the first amount and the second amount may be determined. In some embodiments, the normalized parameter may include the second amount divided by the first amount. The normalized parameter may then be a ratio of the number of loci with DNA molecules smaller than a certain size to the number of loci with DNA molecules larger than a certain size. In other embodiments, the normalized parameter may include the second amount divided by the sum of the first amount and the second amount. In these embodiments, the normalized parameter may be the ratio of the number of loci with DNA molecules having a smaller size to the total number of loci. The normalized parameter may also be the reciprocal of any of these calculations. The normalized parameter may be a type of AAD.

In block 1616, method 1600 may include comparing the parameter value to a calibration point that is determined using at least one other sample (e.g., a calibration sample) having a known fetal DNA fraction and a calibration value corresponding to separate measurement of the parameter in the at least one other sample. The calibration point may be one calibration point of a plurality of calibration points. The plurality of calibration points may constitute a calibration curve. The calibration curve may be a curve fitted to data points of known fetal DNA fraction and normalized parameters determined for different biological samples. The calibration curve may be a linear regression of the data points. The calibration curve may have a slope that does not equal 1.

The calibration curve may be determined using a known fetal DNA fraction and a normalized parameter (i.e., a second normalized parameter) from another biological sample determined by a similar method as the normalized parameter (i.e., the first normalized parameter) from the biological sample currently being analyzed. The second normalized parameter may also be determined from operations similar to blocks 1602 to 1614. The number of reads associated with the loci in the data sets from the other biological sample may be about equal to the number of reads in the current biological sample. The number of reads may be within 1×, 5×, or 10× of each other.

In block 1618, a fetal DNA fraction is computed based on the comparison. The fetal DNA fraction may be the fetal DNA fraction in the calibration curve corresponding to the same value of the normalized parameter. In some embodiments, the fetal DNA fraction may be interpolated between two fetal DNA fractions for two values of the normalized parameter. In other embodiments, the calibration curve may be a linear equation, of the form y=mx+b, where y is the fetal DNA fraction, x is the normalized parameter, and m and b are parameters fitted to the calibration curve.

III. Further Embodiments

Embodiment 1 includes a method of measuring a fetal DNA fraction in a biological sample of a female pregnant with a fetus, the biological sample including maternal DNA molecules and fetal DNA molecules, the method comprising: obtaining a plurality of reads from DNA molecules of the biological sample; identifying a plurality of sites at which the female is homozygous; determining a first amount of reads that exhibit a non-maternal allele at the plurality of sites; determining a total amount of reads at the plurality of sites; determining a non-maternal allele fraction from the first amount and the total amount; obtaining a calibration curve that is determined using known fetal DNA fractions and measured non-maternal allele fractions; and computing the fetal DNA fraction using the calibration curve and the non-maternal allele fraction.

Embodiment 2 includes the method of embodiment 1, further comprising: computing the calibration curve by: determining fetal DNA fractions for a plurality of other samples from a plurality of pregnant females; computing non-maternal fractions for the plurality of samples; and fitting the fetal DNA fractions and the non-maternal fractions to a linear function.

Embodiment 3 includes the method of embodiment 2, wherein determining a fetal DNA fraction for another sample includes: identifying a second plurality of sites where the fetus is heterozygous and the pregnant female is homozygous; obtaining a plurality of reads from DNA molecules of the other sample; determining a second amount of reads having a fetal-specific allele at the second plurality of sites; determining a third amount of reads having a shared allele at the second plurality of sites; and determining the fetal DNA fraction using the second amount and the third amount.

Embodiment 4 includes the method of embodiment 1, wherein the non-maternal allele is limited to an allele identified in a database as corresponding to a biallelic site.

Embodiment 5 includes the method of embodiment 1, wherein identifying the plurality of sites at which the female is homozygous includes genotyping a sample of cells from the female.

Embodiment 6 includes the method of embodiment 1, further comprising: receiving the biological sample; and sequencing a plurality of DNA molecules in the biological sample to obtain the reads.

Embodiment 7 includes the method of embodiment 1, further comprising: receiving the biological sample; and analyzing a plurality of DNA molecules in the biological sample using a microarray of probes to obtain the reads.

Embodiment 8 includes a computer product comprising a computer readable medium storing a plurality of instructions for controlling a computer system to perform an operation of any of the methods of embodiments 1-7.

Embodiment 9 includes a system comprising: the computer product of embodiment 8; and one or more processors for executing instructions stored on the computer readable medium.

Embodiment 10 includes a system comprising means for performing any of the methods of embodiments 1-7.

Embodiment 11 includes a system configured to perform any of the methods of embodiments 1-7.

Embodiment 12 includes a system comprising modules that respectively perform the steps of any of the methods of embodiments 1-7.

IV. Computer System

Figure 17:
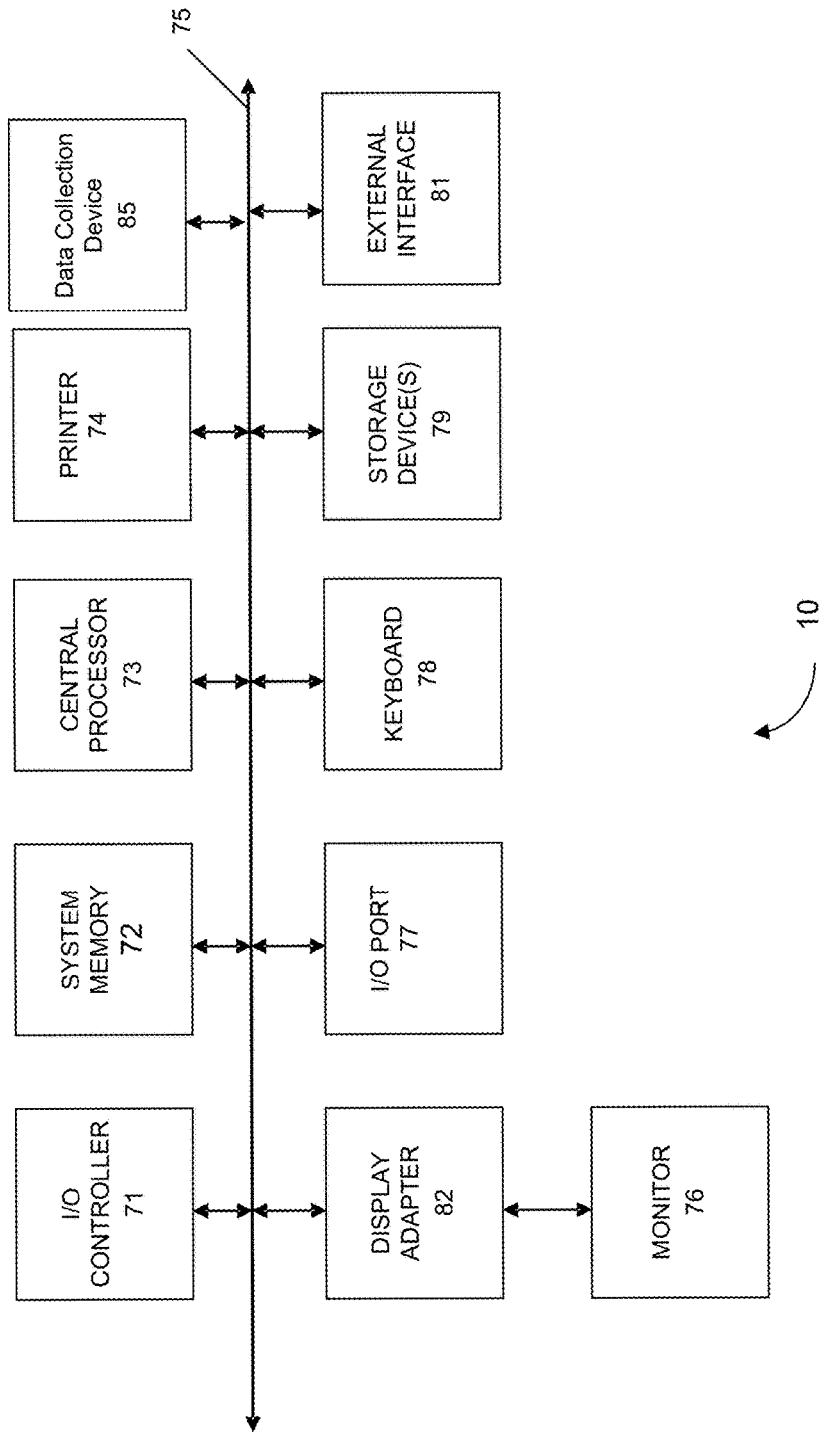
FIG. 17 shows a block diagram of an example computer system usable with system and methods according to embodiments of the present invention.

Any of the computer systems mentioned herein may utilize any suitable number of subsystems. Examples of such subsystems are shown in FIG. 17 in computer system 10. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices.

The subsystems shown in FIG. 17 are interconnected via a system bus 75. Additional subsystems such as a printer 74, keyboard 78, storage device(s) 79, monitor 76, which is coupled to display adapter 82, and others are shown. Peripherals and input/output (I/O) devices, which couple to I/O controller 71, can be connected to the computer system by any number of means known in the art such as input/output (I/O) port 77 (e.g., USB, FireWire®). For example, I/O port 77 or external interface 81 (e.g. Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of instructions from system memory 72 or the storage device(s) 79 (e.g., a fixed disk, such as a hard drive, or optical disk), as well as the exchange of information between subsystems. The system memory 72 and/or the storage device(s) 79 may embody a computer readable medium. Another subsystem is a data collection device 85, such as a camera, microphone, accelerometer, and the like. Any of the data mentioned herein can be output from one component to another component and can be output to the user.

A computer system can include a plurality of the same components or subsystems, e.g., connected together by external interface 81 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. As used herein, a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Figure 18:
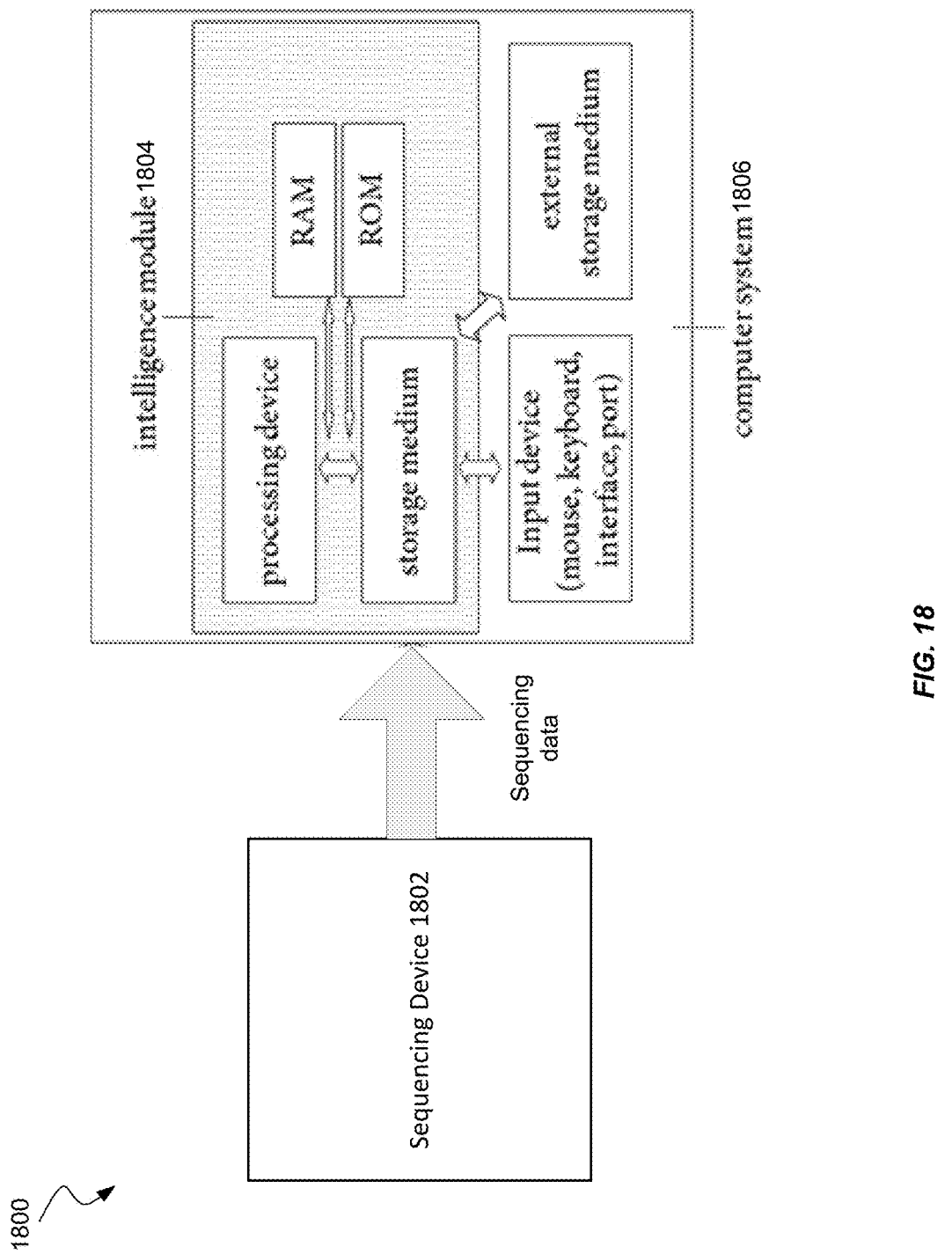
FIG. 18 shows a sequencing system according to embodiments of the present invention.

FIG. 18 shows an exemplary sequencing system. The system depicted in FIG. 18 comprises a sequencing device 1802 and an intelligence module 1804 which is part of the computer system 1806. Sequencing device 1802 may include any sequencing device described herein. Computer system 1806 may include parts or all of computer system 10. The data sets (sequencing reads data sets) are transferred from the sequencing device 1802 to the intelligence module 1804 or vice versa via a network connection or a direct connection. The data sets may for example be processed to identify certain loci. The identification and determination steps may be implemented by software stored on the hardware of computer system 1806. The data sets may be processed by computer code running on the processor and being stored on the storage device of the intelligence module and after processing transferred back to the storage device of the analysis module, where the modified data may be displayed on a displaying device. In some embodiments, the intelligence module may also be implemented in the sequencing device.

Figure 19:
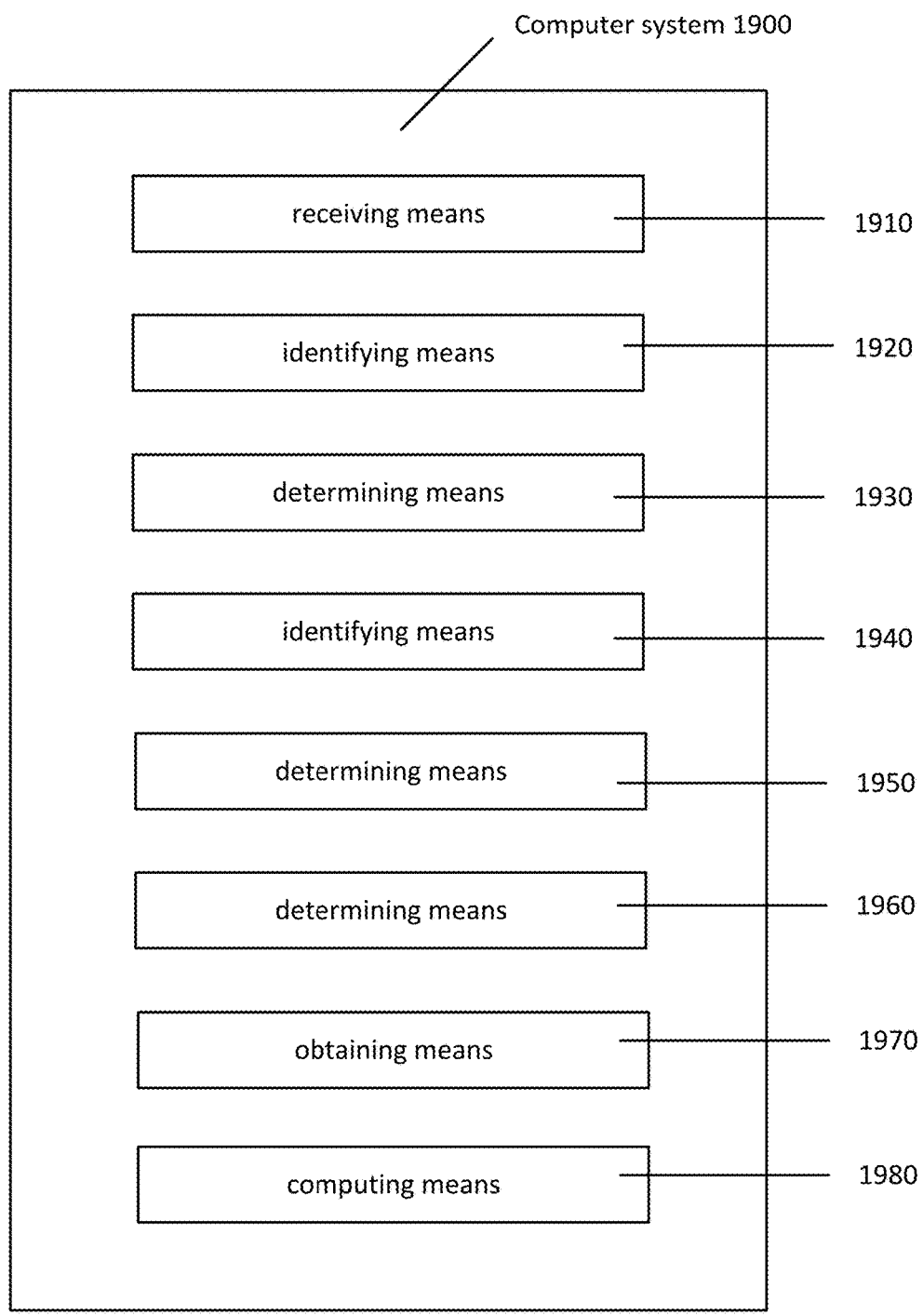
FIG. 19 shows a computer system according to embodiments of the present invention.

FIG. 19 shows that computer system 1900 may comprise receiving means 1910, which may include, for example, receiving sequencing data obtained from a sequencing device. Computer system 1900 may also include identifying means 1920 for identifying a first set of loci in a first data set from a plurality of reads from DNA molecules. Computer system 1900 may also include determining means 1930 for determining a first amount of loci in the first set of loci in the first data set. Computer system 1900 may further include identifying means 1940 for identifying a second set of loci in a second data set from the plurality of reads. Computer system 1900 may also include determining means 1950 for determining a second amount of loci in the second set of loci in the second data set. Computer system 1900 may further include determining means 1960 for determining a normalized parameter of the first amount and the second amount. Computer system 1900 may additionally include obtaining means 1970 for obtaining a calibration point determined using a known fetal DNA fraction. Computer system 1900 may also include computing means 1980 for computing the fetal DNA fraction using the calibration point and the normalized parameter.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, units, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of example embodiments of the invention has been presented for the purposes of illustration and description. It is not intended to be exhaustive or to limit the invention to the precise form described, and many modifications and variations are possible in light of the teaching above.

In the preceding description, for the purposes of explanation, numerous details have been set forth in order to provide an understanding of various embodiments of the present technology. It will be apparent to one skilled in the art, however, that certain embodiments may be practiced without some of these details, or with additional details.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Additionally, details of any specific embodiment may not always be present in variations of that embodiment or may be added to other embodiments.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included.

A recitation of "a", "an" or "the" is intended to mean "one or more" unless specifically indicated to the contrary. The use of "or" is intended to mean an "inclusive or," and not an "exclusive or" unless specifically indicated to the contrary.

All patents, patent applications, publications, and descriptions mentioned herein are incorporated by reference in their entirety for all purposes. None is admitted to be prior art.

What is claimed is:

1. A method of measuring a fetal DNA fraction in a biological sample of a female pregnant with a fetus, the biological sample including maternal DNA molecules and fetal DNA molecules, the method comprising performing, by a computer system:
    identifying a plurality of sites based on sequence information that indicates the female is homozygous for a first allele at each site of the plurality of sites;
    obtaining a plurality of reads from DNA molecules of the biological sample;
    identifying locations of the plurality of reads in a reference genome;
    determining a first value of a first group of DNA molecules based on the plurality of reads, wherein:
        each DNA molecule of the first group of DNA molecules includes a read located at a site of the plurality of sites and exhibits a second allele different from the first allele at the site,
        the first value defines a property of the first group of DNA molecules, and
        a portion of the sites of the plurality of sites do not comprise a read exhibiting a second allele different from the first allele;
    determining a second value of a second group of DNA molecules, wherein:
        each DNA molecule of the second group of DNA molecules includes a read located at a site of the plurality of sites and exhibits the first allele at the site, and
        the second value defines the property of the second group of DNA molecules;
    determining a parameter value of a parameter from the first value and the second value;
    comparing the parameter value to a calibration point that is determined using at least one other sample having a known fetal DNA fraction and a calibration value corresponding to separate measurement of the parameter in the at least one other sample; and
    computing the fetal DNA fraction based on the comparison.

2. The method of claim 1, wherein:
the first value is a first number of reads located at the plurality of sites and having the second allele,
the second value is a second number of reads located at the plurality of sites and having the first allele, and
the parameter is a non-maternal allele fraction.

3. The method of claim 1, wherein determining the first value and the second value further comprises:
    measuring sizes of the first group of DNA molecules and the second group of DNA molecules, wherein the first value is a first size value of a first size distribution of the first group of DNA molecules, and wherein the second value is a second size value of a second size distribution of the second group of DNA molecules.

4. The method of claim 1, wherein:
the plurality of reads is a first plurality of reads,
the biological sample is a first biological sample,
identifying the plurality of sites comprises identifying the plurality of sites from a second plurality of reads from DNA molecules of a second biological sample, and
the second biological sample does not comprise fetal DNA molecules.

5. The method of claim 1, wherein:
the plurality of sites is a first plurality of sites,
the plurality of reads is limited to reads from a second plurality of sites, wherein the second plurality of sites are sites identified in a database as corresponding to a biallelic site.

6. The method of claim 1, wherein the second allele is limited to an allele identified in a database as corresponding to a biallelic site.

7. The method of claim 1, wherein identifying the plurality of sites includes genotyping a sample of cells from the female.

8. The method of claim 1, wherein:
the plurality of reads is a first plurality of reads,
the biological sample is a first biological sample, and
identifying the plurality of sites comprises obtaining a second plurality of reads from DNA molecules of a second biological sample different from the first biological sample.

9. The method of claim 1, wherein:
the plurality of reads is a first plurality of reads, and
identifying the plurality of sites comprises obtaining a second plurality of reads from DNA molecules of the biological sample.

10. The method of claim 1, wherein:
the plurality of sites is a first plurality of sites, and further comprising:
providing a second plurality of sites from a reference database, wherein:
the second plurality of sites comprises sites with known single nucleotide polymorphisms, and
each one of the first plurality of sites is one of the second plurality of sites.

11. The method of claim 1, further comprising:
receiving the biological sample; and
sequencing a plurality of DNA molecules in the biological sample to obtain the reads.

12. The method of claim 1, further comprising:
receiving the biological sample; and
analyzing a plurality of DNA molecules in the biological sample using a microarray of probes to obtain the reads.

13. The method of claim 1, wherein the plurality of reads comprises less than or equal to 50 million reads.

14. The method of claim 1, wherein the plurality of reads is at or less than 1× coverage of a haploid human genome.

15. The method of claim 1, wherein a coverage depth of sequence reads of a dataset is less than 1× coverage.

16. A method of measuring a fetal DNA fraction in a biological sample of a female pregnant with a fetus, the biological sample including maternal DNA molecules and fetal DNA molecules, the method comprising performing, by a computer system:
identifying a plurality of sites based on sequence information that indicates the female is homozygous for a first allele at each site of the plurality of sites;
obtaining a plurality of reads from DNA molecules of the biological sample;
identifying locations of the plurality of reads in a reference genome;
determining a first amount of reads, wherein:
each read of the first amount of reads is located at a site of the plurality of sites,
each read exhibits a second allele different from the first allele at the site, and
a portion of the sites of the plurality of sites do not comprise a read exhibiting a second allele different from the first allele;
determining a second amount of reads at the plurality of sites, wherein:
each read of the second amount of reads is located at a site of the plurality of sites, and
each read exhibits the first allele at the site;
determining a non-maternal allele fraction from the first amount and the second amount;
obtaining a calibration point that is determined using another sample having a known fetal DNA fraction and a measured non-maternal allele fraction; and
computing the fetal DNA fraction using the calibration point and the non-maternal allele fraction.

17. The method of claim 16, wherein determining the second amount of reads at the plurality of sites comprises determining a total number of reads of the plurality of reads, wherein the total number of reads of the plurality of reads is the second amount of reads.

18. The method of claim 16, wherein:
the calibration point is one calibration point of a plurality of calibration points, and
the plurality of calibration points constitutes a calibration curve,
the method further comprising:
computing the calibration curve by:
determining fetal DNA fractions for a plurality of other samples from a plurality of pregnant females;
computing non-maternal allele fractions for the plurality of samples; and
fitting the fetal DNA fractions and the non-maternal allele fractions to a linear function, wherein the linear function describes the calibration curve.

19. The method of claim 18, wherein determining the fetal DNA fraction for each other sample of the plurality of other samples includes:
identifying a second plurality of sites wherein at each site of the second plurality of sites, a pregnant female of the plurality of pregnant females is homozygous and the fetus of the pregnant female is heterozygous;
obtaining a plurality of reads from DNA molecules of the other sample;
determining a third amount of reads exhibiting a fetal-specific allele at the second plurality of sites;
determining a fourth amount of reads exhibiting a shared allele at the second plurality of sites; and
determining the fetal DNA fraction using the third amount and the fourth amount.

20. A method of measuring a fetal DNA fraction in a biological sample of a female pregnant with a fetus, the biological sample including maternal DNA molecules and fetal DNA molecules, the method comprising performing, by a computer system:
identifying a plurality of sites based on sequence information that indicates the female is homozygous for a first allele at each site of the plurality of sites;
obtaining a plurality of reads from DNA molecules of the biological sample;
identifying locations of the plurality of reads in a reference genome;
determining sizes of DNA molecules of the biological sample;
determining a first size value of a first group of DNA molecules, wherein:
each DNA molecule of the first group of DNA molecules includes a read located at a site of the plurality of sites and exhibits a second allele different from the first allele at the site, and
the first size value corresponds to a statistical value of a first size distribution of the first group of DNA molecules;
determining a second size value of a second group of DNA molecules, wherein:
each DNA molecule of the second group of DNA molecules includes a read located at a site of the plurality of sites and exhibits the first allele at the site,
the second size value corresponds to a statistical value of a second size distribution of the second group of DNA molecules, and
a portion of the sites of the plurality of sites do not comprise a read exhibiting a second allele different from the first allele;
determining a parameter value from the first size value and the second size value;

comparing the parameter value to a calibration point that is determined using at least one other sample having a known fetal DNA fraction and a calibration value corresponding to separate measurement of the parameter in the at least one other sample; and computing the fetal DNA fraction based on the comparison.

21. The method of claim 20, wherein:
the first size value is a first cumulative frequency for DNA molecules having a maximum size in the first group of DNA molecules, and
the second size value is a second cumulative frequency for DNA molecules having the maximum size in the second group of DNA molecules.

22. The method of claim 20, wherein:
the first size value is a median size, a mean size, or a mode of the first group of DNA molecules, and
the second size value is a median size, a mean size, or a mode of the second group of DNA molecules.

23. A method for measuring a fetal DNA fraction in a biological sample of a female pregnant with a fetus, the biological sample including maternal DNA molecules and fetal DNA molecules, the method comprising:
receiving a first data set including a first plurality of reads from DNA molecules of a first sample of the female pregnant with the fetus;
identifying locations of the first plurality of reads in a reference genome;
identifying a first set of loci based on the first data set and the identified locations, wherein no locus of the first set of loci exhibits more than one allele;
determining a first amount of loci in the first set of loci;
receiving a second data set including a second plurality of reads from DNA molecules of the biological sample;
identifying locations of the second plurality of reads in the reference genome;
identifying a second set of loci based on the second data set and the identified locations, wherein:
each one of the second set of loci is one of the first set of loci,
each locus of the second set of loci exhibits an allele different from the allele exhibited in the first set of loci, and
a third set of loci of the second plurality of reads do not comprise a read exhibiting an allele different from the allele exhibited in the first set of loci;
determining a second amount of loci in the second set of loci in the second data set;
determining a normalized parameter of the first amount and the second amount;
comparing the parameter value to a calibration point that is determined using at least one other sample having a known fetal DNA fraction and a calibration value corresponding to separate measurement of the parameter in the at least one other sample; and
computing the fetal DNA fraction based on the comparison.

24. The method of claim 23, wherein the first sample is the biological sample.

25. The method of claim 23, wherein the first sample is not the biological sample, and wherein the first sample does not include fetal DNA molecules.

26. The method of claim 23, wherein the allele different from the allele exhibited in the first set of loci is limited to an allele identified in a database as corresponding to a biallelic site.

27. The method of claim 23, wherein the first amount is a number of loci, and the second amount is a number of loci in the second data set.

28. The method of claim 23, further comprising:
measuring sizes of the first plurality of DNA molecules, and
measuring sizes of the second plurality of DNA molecules,
wherein:
the first plurality of DNA molecules have a first size value,
the first size value corresponds to a statistical value of a first size distribution of the first plurality of DNA molecules,
the second plurality of DNA molecules have a second size value,
the second size value corresponds to a statistical value of a second size distribution of the second plurality of DNA molecules, and
the first size value is larger than the second size value by a minimum difference.

29. The method of claim 23, wherein:
a first plurality of DNA molecules comprising reads located at the first set of loci are larger than a first size,
a second plurality of DNA molecules comprising reads located at the second set of loci are smaller than a second size, and
a difference between the first size and the second size is greater than a minimum difference.

30. The method of claim 29, wherein the minimum difference is 5 bp.

31. The method of claim 23, wherein the female is pregnant with a plurality of fetuses, the method further comprising:
comparing the fetal DNA fraction with a cutoff value, and either:
classifying the plurality of fetuses as monozygotic if the computed fetal DNA fraction is below the cutoff value, or
classifying the plurality of fetuses as dizyogitc if the computed fetal DNA fraction is above the cutoff value.

32. The method of claim 31, wherein:
the fetal DNA fraction is a first fetal DNA fraction,
the cutoff value is determined as a value greater than a second fetal DNA fraction of the biological sample, and
the second fetal DNA fraction is determined without using the normalized parameter.

33. The method of claim 32, wherein the second fetal DNA fraction is estimated using a size profile of DNA molecules in the biological sample.

34. The method of claim 23, wherein the first data set comprises reads from DNA molecules of the biological sample.

35. The method of claim 23, wherein:
the biological sample is a first biological sample, and
the first data set comprises reads from DNA molecules of a second biological sample that does not comprise fetal DNA.

36. The method of claim 23, wherein the normalized parameter comprises the second amount divided by the first amount, or wherein the normalized parameter comprises the second amount divided by a sum of the first amount and the second amount.

37. The method of claim 23, wherein:
the calibration point is one calibration point of a plurality of calibration points, the plurality of calibration points constitutes a calibration curve, the normalized parameter is a first normalized parameter, the biological sample is a first biological sample, the calibration point was determined using the known fetal DNA fraction and a second normalized parameter determined from sets of loci in data sets from a third plurality of reads from DNA molecules of a second biological sample in a corresponding method as the first normalized parameter, and the second plurality of reads comprises a first coverage of a haploid human genome is within 10× coverage of a second coverage of reads for the second plurality of reads.

38. The method of claim 23, further comprising:

providing a third set of loci from a reference database, wherein:

the third set of loci comprises loci with known single nucleotide polymorphisms, and each one of the first set of loci is one of the third set of loci.

39. The method of claim 1, wherein the plurality of reads comprises at least 1 million reads.

40. A computer product comprising a non-transitory computer readable medium storing a plurality of instructions for controlling a computer system to perform:

identifying a plurality of sites based on sequence information that indicates a female pregnant with a fetus is homozygous for a first allele at each site of the plurality of sites;

obtaining a plurality of reads from DNA molecules of a biological sample, wherein the biological sample is of the female pregnant with the fetus, and wherein the biological sample includes maternal DNA molecules and fetal DNA molecules;

identifying locations of the plurality of reads in a reference genome;

determining a first value of a first group of DNA molecules based on the plurality of reads, wherein:

each DNA molecule of the first group of DNA molecules includes a read located at a site of the plurality of sites and exhibits a second allele different from the first allele at the site, the first value defines a property of the first group of DNA molecules, and a portion of the sites of the plurality of sites do not comprise a read exhibiting a second allele different from the first allele;

determining a second value of a second group of DNA molecules, wherein:

each DNA molecule of the second group of DNA molecules includes a read located at a site of the plurality of sites and exhibits the first allele at the site, and the second value defines the property of the second group of DNA molecules;

determining a parameter value of a parameter from the first value and the second value;

comparing the parameter value to a calibration point that is determined using at least one other sample having a known fetal DNA fraction and a calibration value corresponding to separate measurement of the parameter in the at least one other sample; and computing the fetal DNA fraction based on the comparison.

41. The computer product of claim 40, wherein:

the first value is a first number of reads located at the plurality of sites and having the second allele, the second value is a second number of reads located at the plurality of sites and having the first allele, and the parameter is a non-maternal allele fraction.

42. The computer product of claim 40, wherein determining the first value and the second value further comprises:

measuring sizes of the first group of DNA molecules and the second group of DNA molecules, wherein the first value is a first size value of a first size distribution of the first group of DNA molecules, and wherein the second value is a second size value of a second size distribution of the second group of DNA molecules.

43. A computer product comprising a non-transitory computer readable medium storing a plurality of instructions for controlling a computer system to perform:

identifying a plurality of sites based on sequence information that indicates a female pregnant with a fetus is homozygous for a first allele at each site of the plurality of sites;

obtaining a plurality of reads from DNA molecules of a biological sample, wherein the biological sample is of the female pregnant with the fetus, and wherein the biological sample includes maternal DNA molecules and fetal DNA molecules;

identifying locations of the plurality of reads in a reference genome;

determining a first amount of reads, wherein:

each read of the first amount of reads is located at a site of the plurality of sites, each read exhibits a second allele different from the first allele at the site, and a portion of the sites of the plurality of sites do not comprise a read exhibiting a second allele different from the first allele;

determining a second amount of reads at the plurality of sites, wherein:

each read of the second amount of reads is located at a site of the plurality of sites, and each read exhibits the first allele at the site;

determining a non-maternal allele fraction from the first amount and the second amount;

obtaining a calibration point that is determined using another sample having a known fetal DNA fraction and a measured non-maternal allele fraction; and computing the fetal DNA fraction using the calibration point and the non-maternal allele fraction.

44. A computer product comprising a non-transitory computer readable medium storing a plurality of instructions for controlling a computer system to perform:

identifying a plurality of sites based on sequence information that indicates a female pregnant with a fetus is homozygous for a first allele at each site of the plurality of sites;

obtaining a plurality of reads from DNA molecules of a biological sample, wherein the biological sample is of the female pregnant with the fetus, and wherein the biological sample includes maternal DNA molecules and fetal DNA molecules;

identifying locations of the plurality of reads in a reference genome;

determining sizes of DNA molecules of the biological sample;

determining a first size value of a first group of DNA molecules, wherein:

each DNA molecule of the first group of DNA molecules includes a read located at a site of the plurality of sites and exhibits a second allele different from the first allele at the site, and the first size value corresponds to a statistical value of a first size distribution of the first group of DNA molecules;

determining a second size value of a second group of DNA molecules, wherein:

each DNA molecule of the second group of DNA molecules includes a read located at a site of the plurality of sites and exhibits the first allele at the site, the second size value corresponds to a statistical value of a second size distribution of the second group of DNA molecules, and a portion of the sites of the plurality of sites do not comprise a read exhibiting a second allele different from the first allele;

determining a parameter value from the first size value and the second size value;

comparing the parameter value to a calibration point that is determined using at least one other sample having a known fetal DNA fraction and a calibration value corresponding to separate measurement of the parameter in the at least one other sample; and computing the fetal DNA fraction based on the comparison.

45. A computer product comprising a non-transitory computer readable medium storing a plurality of instructions for controlling a computer system to perform:

receiving a first data set including a first plurality of reads from DNA molecules of a first sample of a female pregnant with a fetus;

identifying locations of the first plurality of reads in a reference genome;

identifying a first set of loci based on the first data set and the identified locations, wherein no locus of the first set of loci exhibits more than one allele;

determining a first amount of loci in the first set of loci;

receiving a second data set including a second plurality of reads from DNA molecules of a biological sample, wherein the biological sample is of the female pregnant with the fetus, and wherein the biological sample includes maternal DNA molecules and fetal DNA molecules;

identifying locations of the second plurality of reads in the reference genome;

identifying a second set of loci based on the second data set and the identified locations, wherein:

each one of the second set of loci is one of the first set of loci, each locus of the second set of loci exhibits an allele different from the allele exhibited in the first set of loci, and a third set of loci of the second plurality of reads do not comprise a read exhibiting an allele different from the allele exhibited in the first set of loci;

determining a second amount of loci in the second set of loci in the second data set;

determining a normalized parameter of the first amount and the second amount;

comparing the parameter value to a calibration point that is determined using at least one other sample having a known fetal DNA fraction and a calibration value corresponding to separate measurement of the parameter in the at least one other sample; and computing the fetal DNA fraction based on the comparison.

* * * * *